(12) United States Patent
Walter

(10) Patent No.: US 12,344,837 B2
(45) Date of Patent: Jul. 1, 2025

(54) GENE-DRIVE IN DNA VIRUSES

(71) Applicant: Buck Institute for Research on Aging, Novato, CA (US)

(72) Inventor: Marius Walter, San Francisco, CA (US)

(73) Assignee: BUCK INSTITUTE FOR RESEARCH ON AGING, Novato, CA (US)

( * ) Notice: Subject to any disclaimer, the term of this patent is extended or adjusted under 35 U.S.C. 154(b) by 1238 days.

(21) Appl. No.: 17/054,760

(22) PCT Filed: May 28, 2019

(86) PCT No.: PCT/US2019/034205
§ 371 (c)(1),
(2) Date: Nov. 11, 2020

(87) PCT Pub. No.: WO2019/231929
PCT Pub. Date: Dec. 5, 2019

(65) Prior Publication Data
US 2021/0222150 A1    Jul. 22, 2021

Related U.S. Application Data

(60) Provisional application No. 62/677,591, filed on May 29, 2018.

(51) Int. Cl.
| | |
|---|---|
| C12N 15/10 | (2006.01) |
| C12N 7/00 | (2006.01) |
| C12N 9/22 | (2006.01) |
| C12N 15/113 | (2010.01) |

(52) U.S. Cl.
CPC ............ *C12N 15/102* (2013.01); *C12N 7/00* (2013.01); *C12N 9/22* (2013.01); *C12N 15/113* (2013.01); *C12N 2310/20* (2017.05); *C12N 2710/16021* (2013.01); *C12N 2710/16022* (2013.01); *C12N 2710/16121* (2013.01); *C12N 2710/16122* (2013.01)

(58) Field of Classification Search
CPC .......... C12N 15/102; C12N 7/00; C12N 9/22; C12N 15/113; C12N 2310/20; C12N 2710/16021; C12N 2710/16022; C12N 2710/16121; C12N 2710/16122
See application file for complete search history.

(56) References Cited

U.S. PATENT DOCUMENTS

| | | |
|---|---|---|
| 6,291,246 B1 | 9/2001 | Delecluse et al. |
| 2005/0272030 A1 | 12/2005 | Braun |
| 2016/0333376 A1 | 11/2016 | Esvelt et al. |

FOREIGN PATENT DOCUMENTS

| | | | |
|---|---|---|---|
| WO | WO-2015105928 A1 | 7/2015 | |
| WO | WO-2017049266 A2 * | 3/2017 | ......... A01K 67/0339 |

OTHER PUBLICATIONS

Min, J., et al., "Harnessing gene drive," Journal of Responsible Innovation 5(1): S40-S65. Jan. 24, 2018. (Year: 2018).*
Louten, Chapter 4—Virus Replication, Essential Human Virology, Jennifer Louten, Ed., Academic Press. doi.org/10.1016/B978-0-12-800947-5.00004-1. (Year: 2016).*
Li, Z., et al., "CRISPR-Cas9 system-driven site-specific selection pressure on Herpes simplex virus genomes," Virus Res 244: 286-295. doi: 10.1016/j.virusres.2017.03.010. Epub Mar. 6, 2017. (Year: 2017).*
Shi, B. J., et al., Nucleic Acids Res 36(4): 1057-1071. doi: 10.1093/nar/gkm1036. Epub Dec. 17, 2007. (Year: 2007).*
Champer J et al., "Cheating Evolution: Engineering Gene Drives to Manipulate the Fate of Wild Populations," Nature Reviews Genetics, 2016, vol. 17, pp. 146-159.
Chen Y C., et al., "Potential Application of the CRISPR/Cas9 System against Herpesvirus Infections," Viruses. May 29, 2018, vol. 10(6), pp. 1-12.
Esvelt K M., et al., Concerning RNA-guided Gene Drives for the Alteration of Wild Populations, eLife, 2014, vol. 3, e03401, 21 pages.
International Preliminary Report on Patentability dated Dec. 10, 2020, in Application No. PCT/US2019/034205.
International Search Report and Written Opinion dated Sep. 26, 2019, in Application No. PCT/US2019/034205.
Phelan A., et al., "Nuclear Sites of Herpes Simplex Virus Type 1 Dna Replication and Transcription Colocalize at Early Times Postinfection and Are Largely Distinct from RNA Processing Factors," Journal of Virology, Feb. 1, 1997, vol. 71(2), pp. 1124-1132.
Raoult D., et al., "The 1.2-megabase genome sequence of Mimivirus," Science, Oct. 14, 2004, vol. 306(5700), pp. 1344-1350.
Walter M et al., "Viral gene drive in herpesviruses," Nature Communications, 2020, vol. 11, 4884, 11 pages.

* cited by examiner

*Primary Examiner* — Tracy Vivlemore
*Assistant Examiner* — Eric J Rogers
(74) *Attorney, Agent, or Firm* — MINTZ, LEVIN, COHN, FERRIS, GLOVSKY AND POPEO, P.C.

(57) ABSTRACT

In various embodiments methods of utilizing gene drive constructs in asexual organisms such as viruses are provided. In certain embodiments the methods involve transfecting or infecting a cell with a modified DNA virus containing a gene drive construct; and infecting the cell with the target virus where the genome of said target DNA virus is modified by insertion of the gene drive construct into the genome of the target DNA virus and a population of modified target viruses (containing the gene drive construct) is produced.

17 Claims, 10 Drawing Sheets
Specification includes a Sequence Listing.

A

B

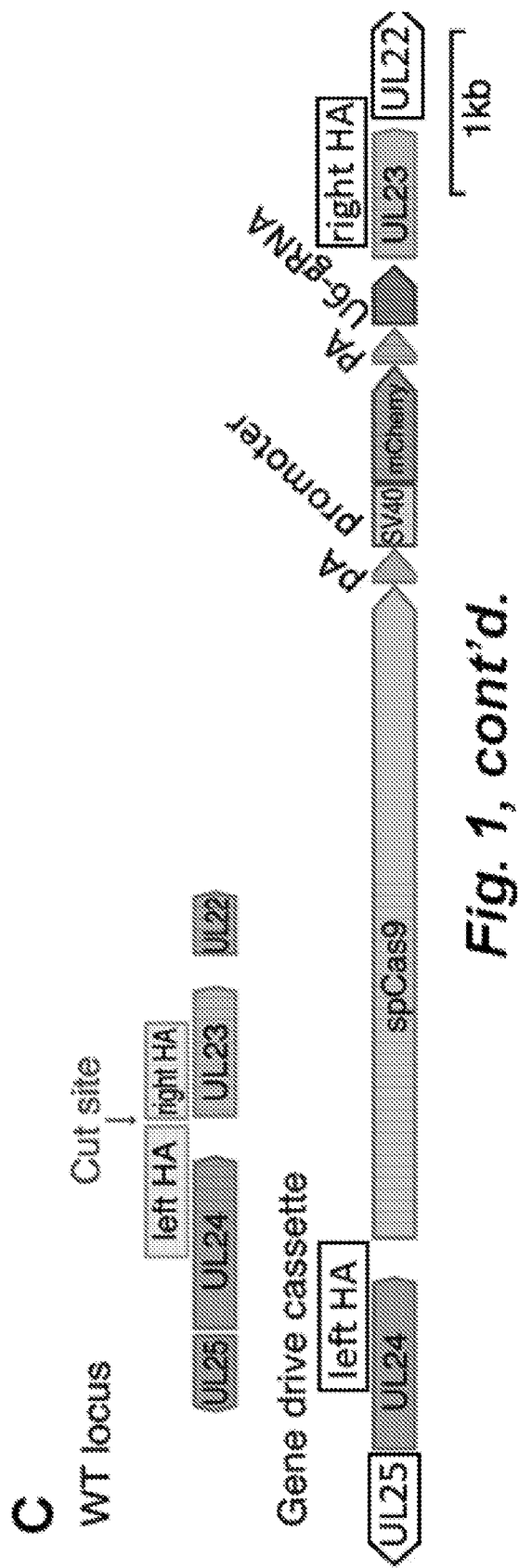
*Fig. 1, cont'd.*

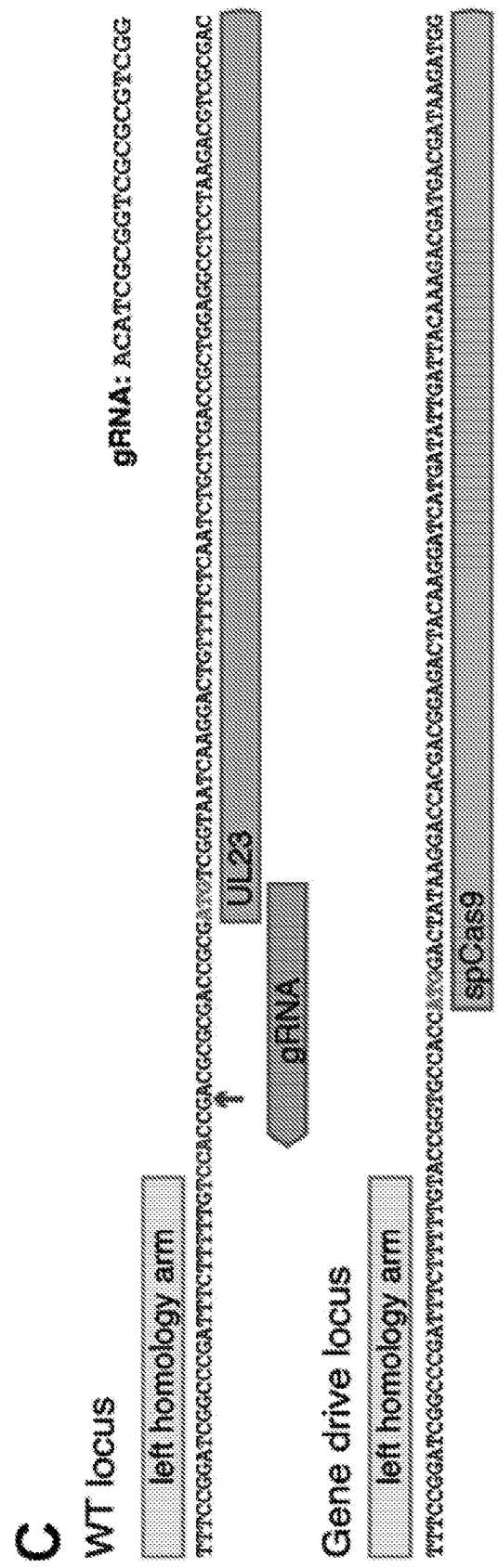
Fig. 2, cont'd.

A

B

C

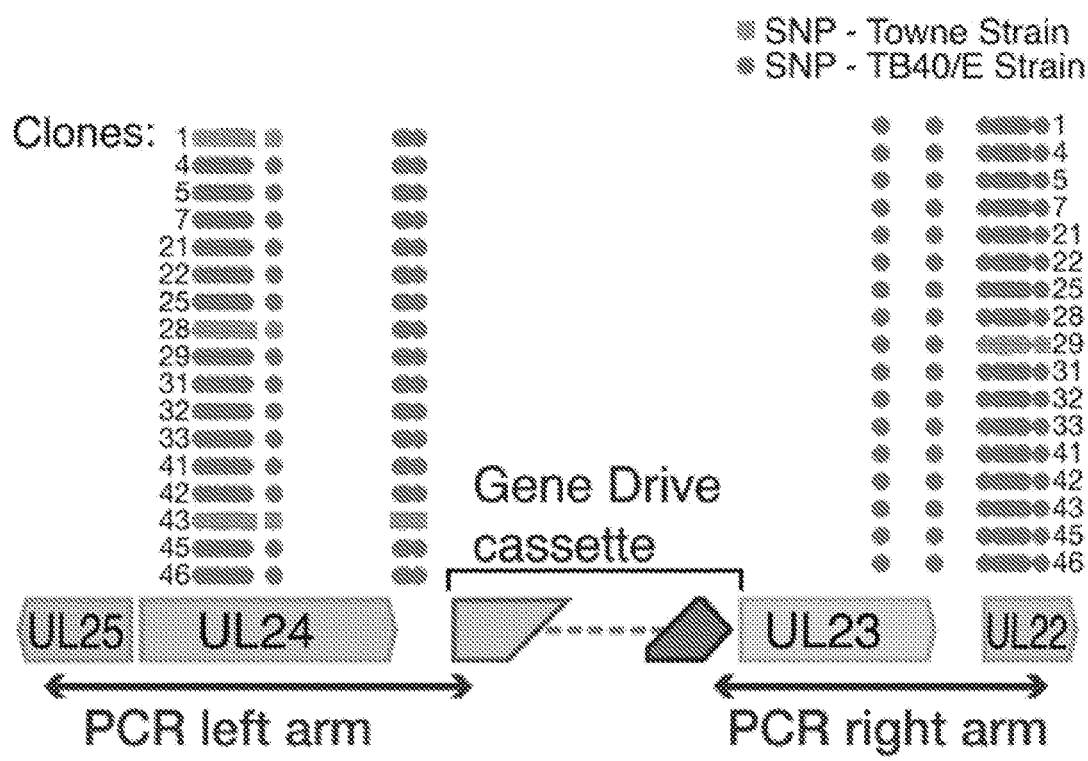
*Fig. 3, cont'd.*

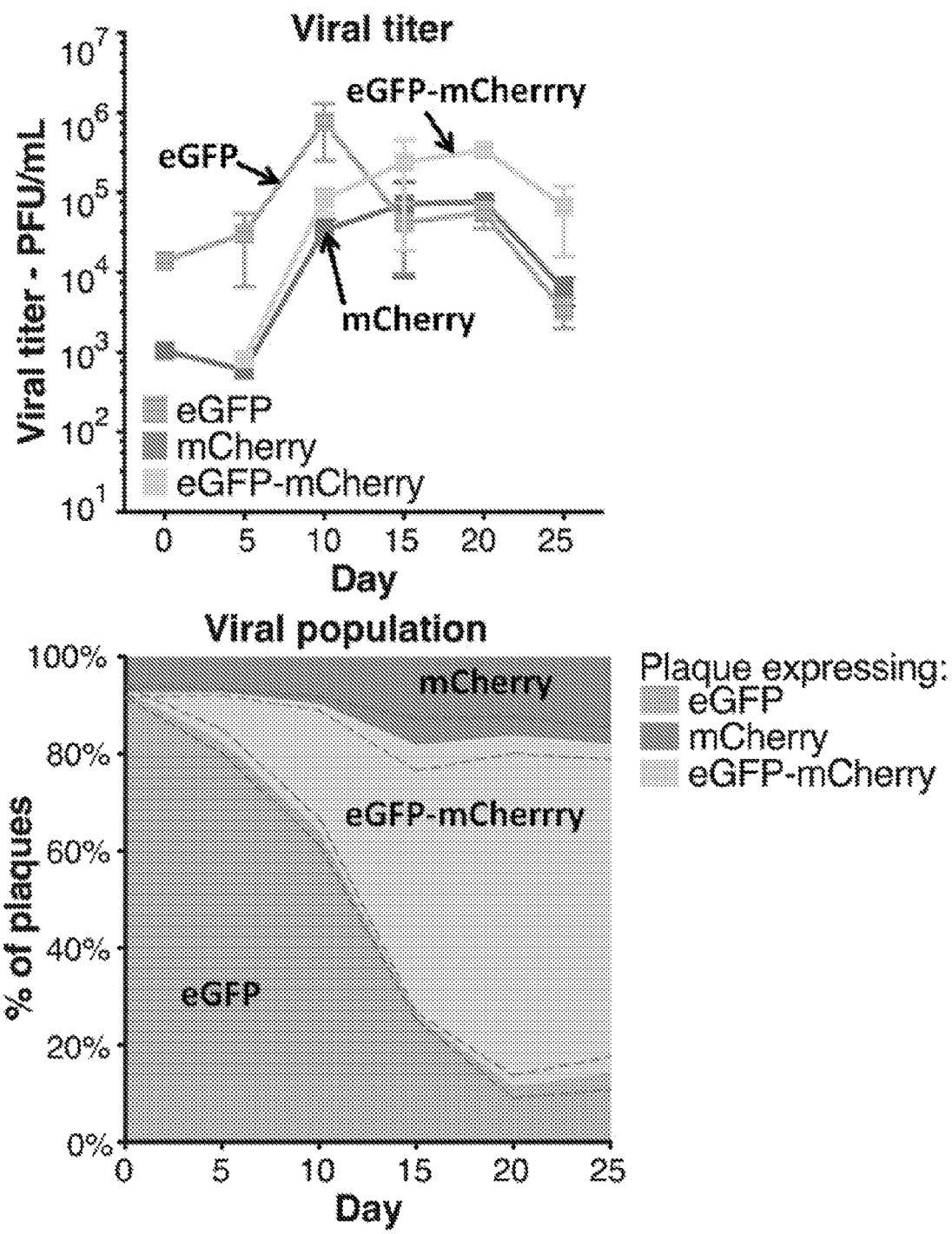
*Fig. 3, cont'd.*

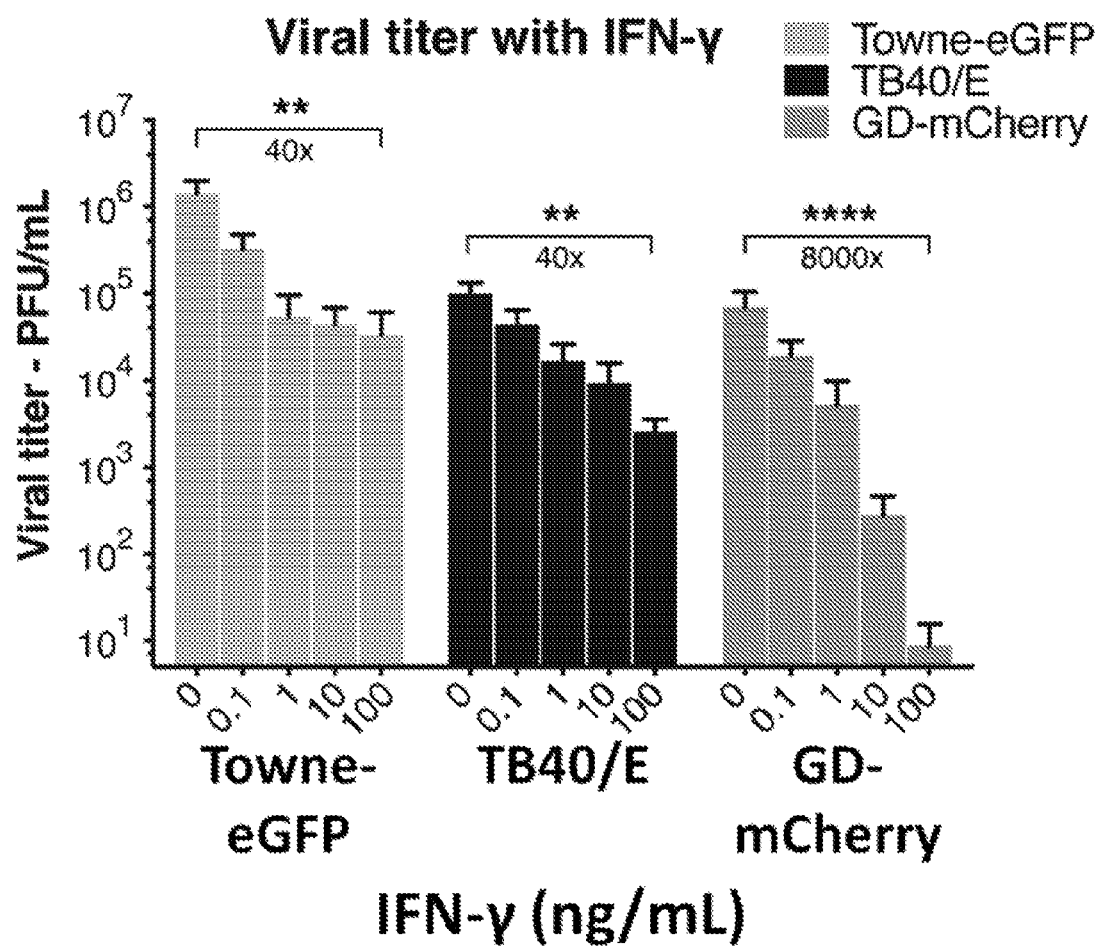
Fig. 3, cont'd.

GENE-DRIVE IN DNA VIRUSES

CROSS-REFERENCE TO RELATED APPLICATIONS

This application is a U.S. 371 National Phase of PCT/US2019/034205, filed on May 28, 2019, which claims priority to and benefit of U.S. Ser. No. 62/677,591, filed on May 29, 2018, both of which are incorporated herein by reference in its entirety for all purposes.

INCORPORATION BY REFERENCE OF SEQUENCE LISTING PROVIDED AS A TEXT FILE

This application contains references to nucleic acid sequences that have been submitted concurrently herewith as the sequence listing text file "BUCK-P062US_ST25.txt", file size 4,012 bytes, created on Jun. 12, 2021, which is incorporated by reference in its entirety pursuant to 37 C.F.R. § 1.52(e)(5).

BACKGROUND

In recent years, CRISPR-Cas9 technology enabled the development of numerous genome-editing strategies (see, e.g., Jinek & Chylinski (2012) *Science,* 337: 816-821; Barrangou & Doudna (2016) *Nat. Biotechnol.* 34: 933-941; Wang et al. (2013) *Cell,* 153: 910-918). Cas9 protein in complex with a guide RNA (gRNA) act by targeting and cleaving a complementary DNA sequence. Cells subsequently repair DNA double-strand breaks, either by Non-homologous end joining, or by homology directed repair (HDR) using a homologous repair template. Gene drive refers to the transmission of specific genetic sequences from one generation to the next with a high probability, and is capable of spreading a trait throughout an entire population (see, e.g., Esvelt et al. (2014) *Elife,* 3: e03401; Champer et al. (2016) *Nat. Rev. Genet.* 17: 146-159). In particular, the possibility to alter populations of mosquitos has received considerable attention, as it could represent a strategy to globally eradicate malaria and other mosquito-borne diseases. Most engineered gene drives use CRISPR-Cas9 editing, where a Cas9 transgene is inserted in place of a natural sequence, alongside a guide RNA targeting this very location. During sexual reproduction, repair of an unmodified allele by homologous recombination after cleavage by Cas9 leads to the duplication of the synthetic sequence, ensuring its propagation through the population (FIG. 1, panel A). Current gene drive strategies can only be implemented in sexually reproducing organisms; therefore, it was thought that gene drives could not be engineered in asexual organisms, such as bacteria and viruses.

SUMMARY

Gene drive refers to genetic sequences that are transmitted from one generation to the next with a high probability, and that are capable of spreading a given trait to an entire population. Most engineered gene drive system use CRISPR-Cas9 editing to duplicate a synthetic sequence from one modified chromosome to its wild-type counterpart during sexual reproduction. Importantly, current gene drive strategies only work in sexually reproducing organisms such as animals but cannot be applied to asexual populations such as viruses and bacteria.

Here however we designed a novel gene drive system that allows the spreading of an engineered trait in populations of DNA viruses, and in particular herpesviruses. We describe the successful transmission of a gene drive sequence between distinct strains of human Cytomegalovirus (Human Herpesvirus 5), and showed that gene drive viruses can efficiently target and replace wildtype populations in cell culture experiments. Our results indicate that viral gene drive can be used to block or drastically circumvent viral infection, which represents a novel therapeutic strategy against herpesviruses and other DNA viruses.

Accordingly, various embodiments contemplated herein may include, but need not be limited to, one or more of the following:

Embodiment 1: A method of modifying a target DNA virus, said method comprising:
    transfecting or infecting a cell population with a modified DNA virus containing a gene drive construct; and
    infecting said cells with said target virus where the genome of said target DNA virus is modified by insertion of said gene drive construct into the genome of said target DNA virus and a population of modified target viruses is produced.

Embodiment 2: The method of embodiment 1, wherein said DNA virus comprises a genome large enough to add a 6-7 kb gene drive sequence.

Embodiment 3: The method of embodiment 2, wherein said virus has a minimal viral genome size of about 50 kb.

Embodiment 4: The method according to any one of embodiments 1-3, wherein said virus has the capacity to undergo homologous recombination.

Embodiment 5: The method of embodiment 4, wherein said virus comprise a nuclear-replicating virus.

Embodiment 6: The method of embodiment 1, wherein said target DNA virus and said modified DNA virus are from a viral family selected from the group consisting of Herpesviridae, Alloherpesviridae, Malacoherpesviridae, Lipothrixviridae, Rudiviridae, Adenoviridae, Ampullaviridae, Ascoviridae, Asfarviridae, Baculoviridae, Bicaudaviridae, Clavaviridae, Corticoviridae, Fuselloviridae, Globuloviridae, Guttaviridae, Hytrosaviridae, Iridoviridae, Lavidaviridae, Marseilleviridae, Mimiviridae, Nudiviridae, Nimaviridae, Pandoraviridae, Papillomaviridae, Phycodnaviridae, Plasmaviridae, Polydnaviruses, Polyomaviridae, Poxviridae, Sphaerolipoviridae, Tectiviridae, and Turriviridae.

Embodiment 7: The method of embodiment 6, wherein said target DNA virus and said modified DNA virus are from the Herpesviridae family.

Embodiment 8: The method of embodiment 7, wherein said target DNA virus and said modified DNA virus are selected from the group consisting of HHV-5 (cytomegalovirus), HHV-1, HHV-2, HHV-3 (varicella-zoster virus (VZV), HHV-4 (Epstein-Barr virus (EBV), HHV-6A and 6B, HHV-7, and HHV-8 (Kaposi's sarcoma-associated herpesvirus (KSHV)), C3Hv, CeHV-1, MuHV-4, SuHV1, BoHV-1, GaHV-1, and MDV.

Embodiment 9: The method of embodiment 8, wherein said target DNA virus and said modified DNA virus are selected from the group consisting of HHV-5 (cytomegalovirus), HHV-1, HHV-2, HHV-3 (varicella-zoster virus (VZV), HHV-4 (Epstein-Barr virus (EBV), HHV-6A and 6B, HHV-7, and HHV-8 (Kaposi's sarcoma-associated herpesvirus (KSHV)).

Embodiment 10: The method of embodiment 8, wherein said target DNA virus and said modified DNA virus are HHV-5.

Embodiment 11: The method of embodiment 1, wherein said target DNA virus and said modified DNA virus are adenovirus.

Embodiment 12: The method of embodiment 1, wherein said target DNA virus and said modified DNA virus are baculovirus.

Embodiment 13: The method of embodiment 1, wherein said target DNA virus and said modified DNA virus are a virus that replicates in the cytoplasm, but encodes its own DNA repair machinery and can undergo homologous recombination in the cytoplasm (e.g., a nucleocytoplasmic large DNA virus).

Embodiment 14: The method of embodiment 1, wherein said target DNA virus and said modified DNA virus are selected from the group consisting of Ascoviridae, Asfarviridae, Poxviridae, Iridoviridae, Marseilleviridae, Megaviridae, Pandoraviridae, Phycodnaviridae, and Pithoviridae.

Embodiment 15: The method of embodiment 14, wherein said target DNA virus and said modified DNA virus is poxvirus or African swine fever virus.

Embodiment 16: The method according to any one of embodiments 1-15, wherein said target DNA virus, before modification, is a wildtype virus.

Embodiment 17: The method according to any one of embodiments 1-16, wherein said gene drive construct comprises: a nucleic acid encoding a targeted endonuclease inserted into the genome of the modified DNA virus at a location corresponding to the location in the target virus that is cleaved by said targeted endonuclease.

Embodiment 18: The method of embodiment 17, wherein said gene drive construct comprises homology arms that permit insertion of said gene drive construct at a site cleaved by said endonuclease.

Embodiment 19: The method of embodiment 18, wherein said homology arms range in length from about 50 bp to about 5 kb.

Embodiment 20: The method according to any one of embodiments 17-19, wherein said targeted endonuclease comprises an endonuclease selected from the group consisting of a class 2 CRISPR/Cas endonuclease, a TALEN, a zinc finger nuclease, and a homing endonuclease.

Embodiment 21: The method of embodiment 20, wherein said targeted endonuclease comprises a class 2 CRISPR/Cas endonuclease and said gene drive construct further comprise a nucleic acid encoding a guide RNA.

Embodiment 22: The method of embodiment 21, wherein said targeted endonuclease comprises a class 2 CRISPR/Cas endonuclease.

Embodiment 23: The method of embodiment 22, wherein said class 2 CRISPR/Cas endonuclease is a type II CRISPR/Cas endonuclease.

Embodiment 24: The method of embodiment 23, wherein the class 2 CRISPR/Cas endonuclease comprises a Cas9 protein.

Embodiment 25: The method of embodiment 24, wherein said Cas9 protein is selected from the group consisting of a *Streptococcus pyogenes* Cas9 protein (spCas9) or a functional portion thereof, a *Staphylococcus aureus* Cas9 protein (saCas9) or a functional portion thereof, a *Streptococcus thermophilus* Cas9 protein (stCas9) or a functional portion thereof, a *Neisseria meningitides* Cas9 protein (nmCas9) or a functional portion thereof, and a *Treponema denticola* Cas9 protein (tdCas9) or a functional portion thereof.

Embodiment 26: The method of embodiment 25, wherein said Cas9 protein comprises a *Streptococcus pyogenes* Cas9 protein (spCas9).

Embodiment 27: The method of embodiment 25, wherein said Cas9 protein comprises a *Staphylococcus aureus* Cas9 protein (saCas9).

Embodiment 28: The method of embodiment 25, wherein said Cas9 protein comprises a *Streptococcus thermophilus* Cas9 protein.

Embodiment 29: The method of embodiment 25, wherein said Cas9 protein comprises a *Neisseria meningitides* Cas9 protein (nmCas9).

Embodiment 30: The method of embodiment 25, wherein said Cas9 protein comprises a *Treponema denticola* Cas9 protein (tdCas9).

Embodiment 31: The method of embodiment 22, wherein said class 2 CRISPR/Cas endonuclease is a type V or type VI CRISPR/Cas endonuclease.

Embodiment 32: The method of embodiment 31, wherein the class 2 CRISPR/Cas protein is selected from the group consisting of a Cpf1 polypeptide or a functional portion thereof, a C2c1 polypeptide or a functional portion thereof, a C2c3 polypeptide or a functional portion thereof, and a C2c2 polypeptide or a functional portion thereof.

Embodiment 33: The method of embodiment 32, wherein the class 2 CRISPR/Cas protein comprises a Cpf1 protein.

Embodiment 34: The method according to any one of embodiments 21-33, wherein said gene drive construct encodes at least one guide RNA.

Embodiment 35: The method of embodiment 34, wherein said gene drive construct encodes at least 2, or at least 3, or at least 4, or at least 5 guide RNAs.

Embodiment 36: The method according to any one of embodiments 34-35, wherein said guide RNA directs said targeted endonuclease to a site in the genome of said target virus where cleavage permits integration of said gene drive construct by homologous recombination.

Embodiment 37: The method according to any one of embodiments 1-36, wherein said gene drive construct comprises a promoter operably linked to the nucleic acid encoding said targeted endonuclease.

Embodiment 38: The method according to any one of embodiments 20-37, wherein said nucleic acid encoding a guide RNA is operably linked to a promoter.

Embodiment 39: The method according to any one of embodiments 37-38, wherein the promoter operably linked to the nucleic acid encoding the targeted endonuclease and/or the promoter operably linked to the nucleic acid encoding a guide RNA, when present, comprises a viral promoter.

Embodiment 40: The method according to any one of embodiments 37-39, wherein the promoter operably linked to the nucleic acid encoding the targeted endonuclease comprises a promoter a promoter of a gene that is modified by said gene drive construct.

Embodiment 41: The method according to any one of embodiments 37-40, wherein said promoter comprises a promoter selected from the group consisting of promoter Sv40, U6, H1, MSV-LTR, CMV promoter, RSV-LTR promoter, Ef1a, CAG, CBh, the TK promoter of Herpes virus, and any endogenous viral promoter such as hCMV-UL23-55-75-79-99.

Embodiment 42: The method according to any one of embodiments 1-41, wherein said gene drive construct inserts into and disrupts an essential viral gene.

Embodiment 43: The method of embodiment 42, wherein said gene drive construct inserts into and disrupts a gene essential for viral infection and/or replication.

Embodiment 44: The method according to any one of embodiments 1-43, wherein said gene drive construct inserts into and disrupts a gene shown in Table 2 and Table 3 or an ortholog or homolog thereof.

Embodiment 45: The method according to any one of embodiments 1-43, wherein said gene drive construct inserts into and disrupts a gene selected from the group consisting of hCMV viral genes UL79, UL122, UL99, UL55, UL23, UL75, UL92, UL44, and UL82.

Embodiment 46: The method of embodiment 45, wherein said gene drive construct inserts into and disrupts a gene selected from the group consisting of UL23, UL122, UL79, UL99, and UL55.

Embodiment 47: The method of embodiment 46, wherein said gene drive construct inserts into and disrupts hCMV UL23 gene or a homolog or ortholog thereof.

Embodiment 48: The method of embodiment 47, wherein said method utilizes a gRNA selected from the group consisting of ACATCGCGGTCGCGCGTCGG (SEQ ID NO:14), GTCCTTGATTACCGACATCG (SEQ ID NO:15), TCAATCTGCTCGACCGCTGG (SEQ ID NO:16), and TTCTCAATCTGCTCGACCGC (SEQ ID NO: 14).

Embodiment 49: The method of embodiment 46, wherein said gene drive construct inserts into and disrupts hCMV UL79 gene or a homolog or ortholog thereof.

Embodiment 50: The method of embodiment 49, wherein said method utilizes a gRNA selected from the group consisting of TAGATGATTGGCGCAAGTAA (SEQ ID NO:6), and ATTAGCGAGAAGATGTCGCG (SEQ ID NO:7).

Embodiment 51: The method of embodiment 46, wherein said gene drive construct inserts into and disrupts hCMV UL122 gene or a homolog or ortholog thereof.

Embodiment 52: The method of embodiment 51, wherein said method utilizes a gRNA selected from the group consisting of TTGGAGGAAGGGCCCTCGTC (SEQ ID NO:8), and ATCAGGGTCCATCTTTCTCT (SEQ ID NO:9).

Embodiment 53: The method of embodiment 46, wherein said gene drive construct inserts into and disrupts hCMV UL99 gene or a homolog or ortholog thereof.

Embodiment 54: The method of embodiment 53, wherein said method utilizes a gRNA selected from the group consisting of GCGACCCAGAGCATCTTTCA (SEQ ID NO:10), and CCGACTTCCTCCTCGGACGA (SEQ ID NO:11).

Embodiment 55: The method of embodiment 46, wherein said gene drive construct inserts into and disrupts hCMV UL55 gene or a homolog or ortholog thereof.

Embodiment 56: The method of embodiment 55, wherein said method utilizes a gRNA selected from the group consisting of GGACGACCTCATGAGCGGCC (SEQ ID NO:12), and AAGGCCGTTGGCGTAGCCAT (SEQ ID NO:13).

Embodiment 57: The method of embodiment 46, wherein said gene drive construct inserts into and disrupts hCMV UL75 gene or a homolog or ortholog thereof.

Embodiment 58: The method of embodiment 57, wherein said method utilizes a gRNA comprising the sequence CAAAAAGACATCGAGGCATA (SEQ ID NO:18).

Embodiment 59: The method according to any one of embodiments 1-58, wherein said gene drive introduces a modification that inhibits replication and/or assembly of said virus and said modification is compensated for by expression of said gene by the target virus in said cell to permit viral replication.

Embodiment 60: The method according to any one of embodiments 1-58, wherein said gene drive introduces a modification that inhibits replication and/or assembly of said virus and said modification is compensated for by expression of a rescue gene within said gene drive construct.

Embodiment 61: The method of embodiment 60, wherein said rescue gene is operably linked to an inducible promoter.

Embodiment 62: The method of embodiment 60, wherein said rescue gene is operably linked to a constitutive promoter.

Embodiment 63: The method of embodiment 20, wherein, wherein said targeted endonuclease comprises a zinc finger nuclease.

Embodiment 64: The method of embodiment 20, wherein, wherein said targeted endonuclease comprises a TALEN.

Embodiment 65: The method according to any one of embodiments 1-64, wherein said modified DNA virus and said target virus are introduced into a cell ex vivo.

Embodiment 66: The method of embodiment 65, wherein said cell comprises a mammalian cell.

Embodiment 67: The method of embodiment 66, wherein said cell comprises a cell in a cell line.

Embodiment 68: The method of embodiment 66, wherein said cell comprises a primary cell in culture.

Embodiment 69: The method according to any one of embodiments of embodiments 65-68, wherein said cell comprise a fibroblast.

Embodiment 70: The method according to any one of embodiments of embodiments 65-68, wherein said cell comprises a cell from a cell line selected from the group consisting of 3T3, COS7, N2A, HEK293, HUVEC, Vero, and Hela.

Embodiment 71: The method according to any one of embodiments 1-64, wherein said modified DNA virus and said target virus are introduced into cell in vivo.

Embodiment 72: The method of embodiment 71, wherein said modified DNA virus is introduced into a cell already infected by said target virus.

Embodiment 73: The method according to any one of embodiments 71-72, wherein said method comprises administering said modified DNA virus to a mammal infected with said target virus.

Embodiment 74: The method according to any one of embodiments 71-72, wherein said method comprises administering said modified DNA virus to an animal (e.g., fish, birds, reptiles, amphibians, insects and other arthropods, etc.) already infected with said target virus.

Embodiment 75: The method according to any one of embodiments 71-72, wherein said method comprises administering said modified DNA virus to any eukaryote (plants, algae, fungus, protists) infected with said target virus.

Embodiment 76: The method according to any one of embodiments 71-72, wherein said method comprises administering said modified DNA virus to an individual (any eukaryote) non infected with said virus, as a preventive strategy.

Embodiment 77: A modified DNA virus wherein said DNA virus contains a gene drive construct.

Embodiment 78: The modified virus of embodiment 77, wherein said gene drive construct is integrated into the genome of said DNA virus.

Embodiment 79: The modified virus according to any one of embodiments 77-78, wherein said DNA virus comprises a genome large enough to add a 6-7 kb gene drive sequence.

Embodiment 80: The modified virus of embodiment 79, wherein said virus has a minimal viral genome size of about 50 kb.

Embodiment 81: The modified virus according to any one of embodiments 79-80, wherein said virus has the capacity to undergo homologous recombination.

Embodiment 82: The modified virus of embodiment 81, wherein said virus comprises a nuclear-replicating virus.

Embodiment 83: The modified virus of embodiment 79, wherein said virus is from a viral family selected from the group consisting of Herpesviridae, Alloherpesviridae, Malacoherpesviridae, Lipothrixviridae, Rudiviridae, Adenoviridae, Ampullaviridae, Ascoviridae, Asfarviridae, Baculoviridae, Bicaudaviridae, Clavaviridae, Corticoviridae, Fuselloviridae, Globuloviridae, Guttaviridae, Hytrosaviridae, Iridoviridae, Lavidaviridae, Marseilleviridae, Mimiviridae, Nudiviridae, Nimaviridae, Pandoraviridae, Papillomaviridae, Phycodnaviridae, Plasmaviridae, Polydnaviruses, Polyomaviridae, Poxviridae, Sphaerolipoviridae, Tectiviridae, and Turriviridae.

Embodiment 84: The modified virus of embodiment 83, wherein said virus is from the Herpesviridae family.

Embodiment 85: The modified virus of embodiment 84, wherein said virus is selected from the group consisting of HHV-5 (cytomegalovirus), HHV-1, HHV-2, HHV-3 (varicella-zoster virus (VZV), HHV-4 (Epstein-Barr virus (EBV), HHV-6A and 6B, HHV-7, and HHV-8 (Kaposi's sarcoma-associated herpesvirus (KSHV)), C3Hv, CeHV-1, MuHV-4, SuHV1, BoHV-1, GaHV-1, and MDV.

Embodiment 86: The modified virus of embodiment 85, wherein said virus is selected from the group consisting of HHV-5 (cytomegalovirus), HHV-1, HHV-2, HHV-3 (varicella-zoster virus (VZV), HHV-4 (Epstein-Barr virus (EBV), HHV-6A and 6B, HHV-7, and HHV-8 (Kaposi's sarcoma-associated herpesvirus (KSHV)).

Embodiment 87: The modified virus of embodiment 85, wherein said virus is an HHV-5 virus.

Embodiment 88: The modified virus of embodiment 77, wherein said virus is an adenovirus.

Embodiment 89: The modified virus of embodiment 77, wherein said virus is a baculovirus.

Embodiment 90: The modified virus of embodiment 77, wherein said virus is a virus that replicates in the cytoplasm but encodes its own DNA repair machinery and can undergo homologous recombination in the cytoplasm (e.g., a nucleocytoplasmic large DNA virus).

Embodiment 91: The modified virus of embodiment 90, wherein said virus is selected from the group consisting of Ascoviridae, Poxviridae, Iridoviridae, Marseilleviridae, Megaviridae, Pandoraviridae, Phycodnaviridae, and Pithoviridae.

Embodiment 92: The modified virus of embodiment 91, wherein said virus is a poxvirus or an African Swine fever virus.

Embodiment 93: The modified virus according to any one of embodiments 77-92, wherein said gene drive construct comprises: a nucleic acid encoding a targeted endonuclease inserted into the genome of the modified DNA virus at a location corresponding to the location in the target virus that is cleaved by said targeted endonuclease.

Embodiment 94: The modified virus of embodiment 93, wherein said gene drive construct comprises homology arms that permit insertion of said gene drive construct at a site cleaved by said endonuclease.

Embodiment 95: The modified virus of embodiment 94, wherein said homology arms range in length from about 50 bp to 5000b.

Embodiment 96: The modified virus according to any one of embodiments 93-95, wherein said targeted endonuclease comprises an endonuclease selected from the group consisting of a class 2 CRISPR/Cas endonuclease, a TALEN, a zinc finger nuclease, and a homing endonuclease.

Embodiment 97: The modified virus of embodiment 96, wherein said targeted endonuclease comprises a class 2 CRISPR/Cas endonuclease and said gene drive construct further comprise a nucleic acid encoding a guide RNA.

Embodiment 98: The modified virus of embodiment 97, wherein said targeted endonuclease comprises a class 2 CRISPR/Cas endonuclease.

Embodiment 99: The modified virus of embodiment 98, wherein said class 2 CRISPR/Cas endonuclease is a type II CRISPR/Cas endonuclease.

Embodiment 100: The modified virus of embodiment 99, wherein the class 2 CRISPR/Cas endonuclease comprises a Cas9 protein.

Embodiment 101: The modified virus of embodiment 100, wherein said Cas9 protein is selected from the group consisting of a *Streptococcus pyogenes* Cas9 protein (spCas9) or a functional portion thereof, a *Staphylococcus aureus* Cas9 protein (saCas9) or a functional portion thereof, a *Streptococcus thermophilus* Cas9 protein (stCas9) or a functional portion thereof, a *Neisseria meningitides* Cas9 protein (nmCas9) or a functional portion thereof, and a *Treponema denticola* Cas9 protein (tdCas9) or a functional portion thereof.

Embodiment 102: The modified virus of embodiment 101, wherein said Cas9 protein comprises a *Streptococcus pyogenes* Cas9 protein (spCas9).

Embodiment 103: The modified virus of embodiment 101, wherein said Cas9 protein comprises a *Staphylococcus aureus* Cas9 protein (saCas9).

Embodiment 104: The modified virus of embodiment 101, wherein said Cas9 protein comprises a *Streptococcus thermophilus* Cas9 protein.

Embodiment 105: The modified virus of embodiment 101, wherein said Cas9 protein comprises a *Neisseria meningitides* Cas9 protein (nmCas9).

Embodiment 106: The modified virus of embodiment 101, wherein said Cas9 protein comprises a *Treponema denticola* Cas9 protein (tdCas9).

Embodiment 107: The modified virus of embodiment 98, wherein said class 2 CRISPR/Cas endonuclease is a type V or type VI CRISPR/Cas endonuclease.

Embodiment 108: The modified virus of embodiment 107, wherein the class 2 CRISPR/Cas protein is selected from the group consisting of a Cpf1 polypeptide or a functional portion thereof, a C2c1 polypeptide or a functional portion thereof, a C2c3 polypeptide or a functional portion thereof, and a C2c2 polypeptide or a functional portion thereof.

Embodiment 109: The modified virus of embodiment 108, wherein the class 2 CRISPR/Cas protein comprises a Cpf1 protein.

Embodiment 110: The modified virus according to any one of embodiments 97-109, wherein said gene drive construct encodes at least one guide RNA.

Embodiment 111: The modified virus of embodiment 110, wherein said gene drive construct encodes at least 2, or at least 3, or at least 4, or at least 5 guide RNAs.

Embodiment 112: The modified virus according to any one of embodiments 110-111, wherein said guide RNA directs said targeted endonuclease to a site in the genome of said target virus where cleavage permits integration of said gene drive construct by homologous recombination.

Embodiment 113: The modified virus according to any one of embodiments 77-112, wherein said gene drive construct comprises a promoter operably linked to the nucleic acid encoding said targeted endonuclease.

Embodiment 114: The modified virus according to any one of embodiments 97-113, wherein said nucleic acid encoding a guide RNA is operably linked to a promoter.

Embodiment 115: The modified virus according to any one of embodiments 113-114, wherein the promoter operably linked to the nucleic acid encoding the targeted endonuclease and/or the promoter operably linked to the nucleic acid encoding a guide RNA, when present, comprises a viral promoter.

Embodiment 116: The modified virus according to any one of embodiments 113-115, wherein the promoter operably linked to the nucleic acid encoding the targeted endonuclease comprises a promoter a promoter of a gene that is modified by said gene drive construct.

Embodiment 117: The modified virus according to any one of embodiments 37-116, wherein said promoter comprises a promoter selected from the group consisting of hCMV-UL79, hCMV-UL75, hCMV-UL99, hCMV-UL23 promoter Sv40, U6, H1, MSV-LTR, CMV promoter, RSV-LTR promoter, Ef1a, CAG, CBh, the TK promoter of Herpes virus.

Embodiment 118: The modified virus according to any one of embodiments 77-117, wherein said gene drive construct is inserted into and disrupts an essential viral gene.

Embodiment 119: The modified virus of embodiment 118, wherein said gene drive construct is inserted into and disrupts a gene essential for viral infection and/or replication.

Embodiment 120: The modified virus according to any one of embodiments 77-119, wherein said gene drive construct inserts into and disrupts a gene shown shown in Table 2 and/or Table 3 or an ortholog or homolog thereof.

Embodiment 121: The modified virus according to any one of embodiments 77-119, wherein said gene drive construct inserts into and disrupts a gene selected from the group consisting of UL79, UL122, UL99, UL55, UL23, UL75, UL92, UL44, and UL82.

Embodiment 122: The modified virus of embodiment 121, wherein said gene drive construct inserts into and disrupts a gene selected from the group consisting of UL23, UL122, UL79, UL99, and UL55.

Embodiment 123: The modified virus of embodiment 122, wherein said gene drive construct inserts into and disrupts a UL23 gene or a homolog or ortholog thereof.

Embodiment 124: The modified virus of embodiment 123, wherein said gene drive construct utilizes a gRNA selected from the group consisting of ACATCGCGGTCGCGCGTCGG (SEQ ID NO:14), GTCCTTGATTACCGACATCG (SEQ ID NO:15), TCAATCTGCTCGACCGCTGG (SEQ ID NO:16), and TTCTCAATCTGCTCGACCGC (SEQ ID NO:14).

Embodiment 125: The modified virus of embodiment 122, wherein said gene drive construct inserts into and disrupts a UL79 gene or a homolog or ortholog thereof.

Embodiment 126: The modified virus of embodiment 125, wherein said method utilizes a gRNA selected from the group consisting of TAGATGATTGGCGCAAGTAA (SEQ ID NO:6), and ATTAGCGAGAAGATGTCGCG (SEQ ID NO:7).

Embodiment 127: The modified virus of embodiment 122, wherein said gene drive construct inserts into and disrupts a UL122 gene or a homolog or ortholog thereof.

Embodiment 128: The modified virus of embodiment 127, wherein gene drive construct utilizes a gRNA selected from the group consisting of TTGGAG-GAAGGGCCCTCGTC (SEQ ID NO:8), and ATCAGGGTCCATCTTTCTCT (SEQ ID NO:9).

Embodiment 129: The modified virus of embodiment 122, wherein said gene drive construct inserts into and disrupts a UL99 gene or a homolog or ortholog thereof.

Embodiment 130: The modified virus of embodiment 129, wherein said gene drive construct utilizes a gRNA selected from the group consisting of GCGACCCAGAG-CATCTTTCA (SEQ ID NO:10), and CCGACTTCCTCCTCGGACGA (SEQ ID NO:11).

Embodiment 131: The modified virus of embodiment 122, wherein said gene drive construct inserts into and disrupts a UL55 gene or a homolog or ortholog thereof.

Embodiment 132: The modified virus of embodiment 131, wherein said gene drive construct utilizes a gRNA selected from the group consisting of GGACGACCTCAT-GAGCGGCC (SEQ ID NO: 12), and AAGGCCGTTGGCGTAGCCAT (SEQ ID NO:13).

Embodiment 133: The modified virus of embodiment 122, wherein said gene drive construct inserts into and disrupts a UL75 gene or a homolog or ortholog thereof.

Embodiment 134: The modified virus of embodiment 133, wherein said gene drive construct utilizes a gRNA comprising the sequence CAAAAAGACATCGAGGCATA (SEQ ID NO:18).

Embodiment 135: The modified virus according to any one of embodiments 77-134, wherein said gene drive introduces a modification that inhibits replication and/or assembly of said virus and said modification is compensated for by expression of said gene by the target virus in said cell to permit viral replication.

Embodiment 136: The modified virus according to any one of embodiments 77-134, wherein said gene drive introduces a modification that inhibits replication and/or assembly of said virus and said modification is compensated for by expression of a rescue gene within said gene drive construct.

Embodiment 137: The modified virus of embodiment 136, wherein said rescue gene is operably linked to an inducible promoter.

Embodiment 138: The modified virus of embodiment 136, wherein said rescue gene is operably linked to a constitutive promoter.

Embodiment 139: The modified virus of embodiment 96, wherein, wherein said targeted endonuclease comprises a zinc finger nuclease.

Embodiment 140: The modified virus of embodiment 96, wherein, wherein said targeted endonuclease comprises a TALEN.

Embodiment 141: A cell containing a modified virus according to any one of embodiments 77-140.

Embodiment 142: The cell of embodiment 141, wherein said cell comprises a mammalian cell.

Embodiment 143: The cell of embodiment 142, wherein said cell comprises a cell in a cell line.

Embodiment 144: The cell of embodiment 142, wherein said cell comprises a primary cell in culture.

Embodiment 145: The cell according to any one of embodiments of embodiments 141-144, wherein said cell comprise a fibroblast.

Embodiment 146: The cell of embodiment 143, wherein said cell comprises a cell from a cell line selected from the group consisting of 3T3, COS7, N2A, and HEK293, N2A, HEK293, HUVEC, Vero, Hela.

Embodiment 147: The cell of embodiment 141, wherein said cell comprises a human foreskin fibroblast (HFF) cell.

Definitions

The term "operably linked" refers to functional linkage between a promoter and a second sequence, wherein the promoter sequence initiates transcription of RNA corresponding to the second sequence.

A targeted endonuclease is an endonuclease that cleaves or nicks a at a pre-identified or predetermined location in a target nucleic acid sequence. The endonuclease can be targeted by virtue of its amino acid composition, or, in the case of RNA guided endonucleases by the nucleic acid sequence of the guide RNA.

In class 2 CRISPR systems, the functions of the effector complex (e.g., the cleavage of target DNA) are carried out by a single endonuclease (e.g., see Zetsche et al. (2015) *Cell*, 163(3):759-771; Makarova et al. (2015) *Nat. Rev. Microbiol.* 13(11): 722-736; and Shmakov et al. (2015) *Mol. Cell.* 60(3): 385-397). As such, the term "class 2 CRISPR/Cas protein" is used herein to encompass the endonuclease (the target nucleic acid cleaving protein) from class 2 CRISPR systems. Thus, the term "class 2 CRISPR/Cas endonuclease" as used herein encompasses type II CRISPR/Cas proteins (e.g., Cas9), type V CRISPR/Cas proteins (e.g., Cpf1, C2c1, C2C3), and type VI CRISPR/Cas proteins (e.g., C2c2). To date, class 2 CRISPR/Cas proteins encompass type II, type V, and type VI CRISPR/Cas proteins, but the term is also meant to encompass any class 2 CRISPR/Cas protein suitable for binding to a corresponding guide RNA and forming an RNP complex.

DETAILED DESCRIPTION

Figure 1:
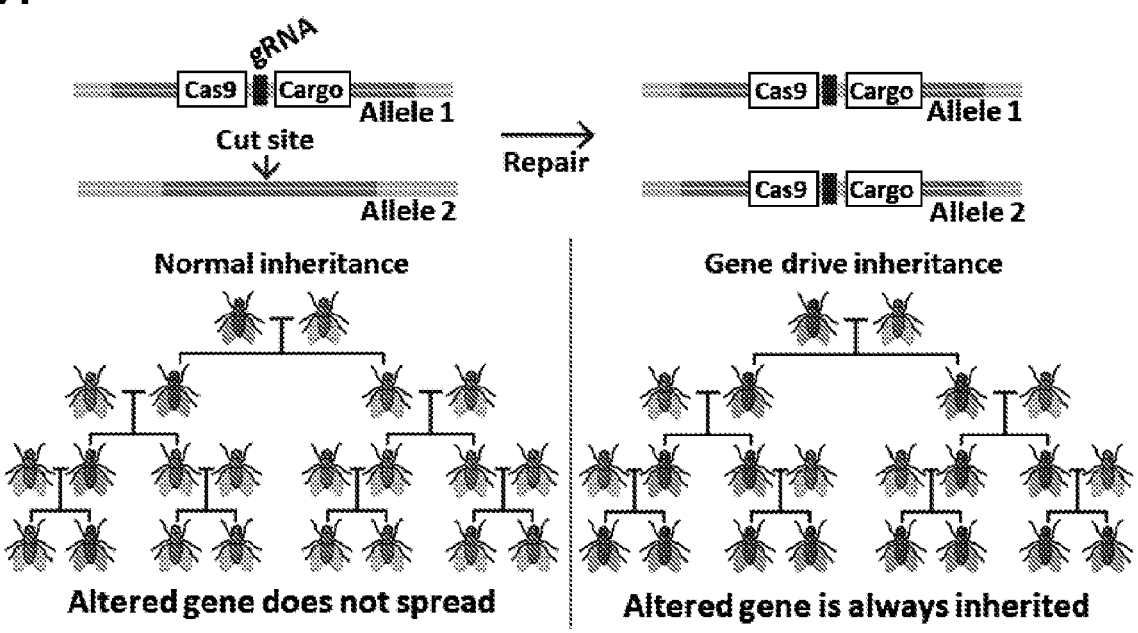
FIG. 1, panels A-C, illustrates gene-drive systems. CRISPR-based gene drive sequences are composed at the minimum of Cas9 and a gRNA targeting the complementary wildtype locus, and can also harbor an additional "cargo" that will be carried over with the rest of the sequence. When present in the same cell nucleus, Cas9 target and cleave the wildtype sequence. Homology directed repair of the damaged wildtype locus using the gene drive sequence as a repair template ensure the conversion of the wildtype locus into a new gene drive sequence. Panel A) In sexually reproducing species, gene drive and wildtype allele are inherited during sexual reproduction from the two parents. Cleavage and repair of the wildtype allele ensure that the gene drive allele is always homozygous. The altered locus is therefore always inherited, ensuring the rapid spread of the modification in the population. Panel B) With herpesviruses, gene drive involves the co-infection of a given cell by a wildtype and a modified virus. Cleavage and repair of the wildtype genome convert the wildtype virus into a new gene drive virus. In this example, hCMV WT genome (Towne strain) express eGFP florescent protein, while gene drive genome (TB40/E strain) carries mCherry. Recombinant viruses then express both eGFP and mCherry. Panel C) Modified and unmodified UL23 locus. The target site is located upstream of UL23 CDS. Gene drive cassette is composed in this order of spCas9, SV40 polyA signal, SV40 promoter, mCherry reporter, Beta-globin polyA signal and a U6-driven gRNA.
Figure 1:
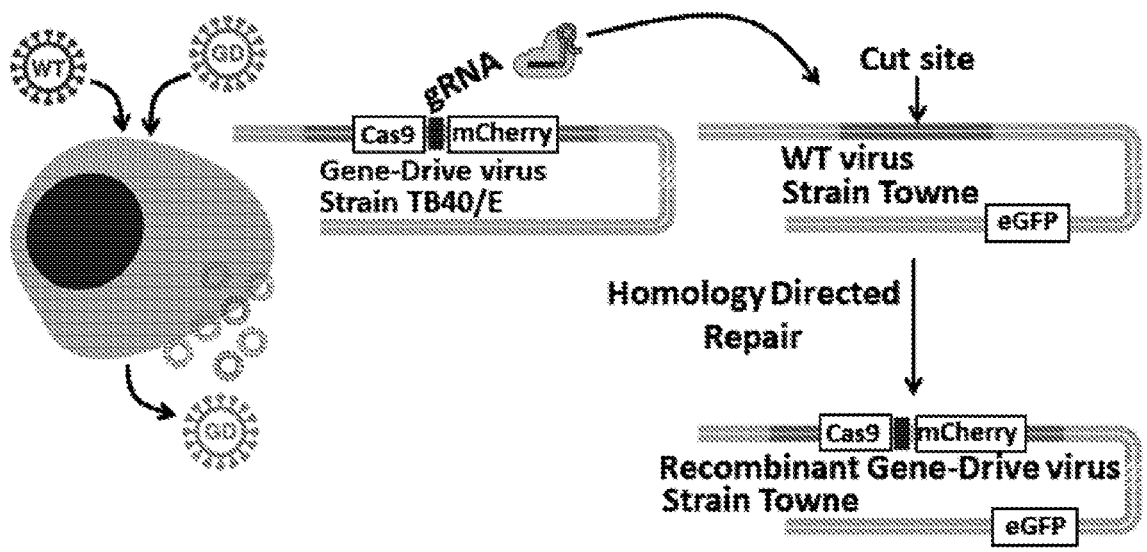

Gene-drive refers to genetic sequences that are transmitted from one generation to the next with a high probability, and that are capable of spreading a given trait to an entire population. Natural homing endonuclease genes exhibit gene drive by cutting the corresponding locus of chromosomes lacking them. This induces the cell to repair the break by copying the nuclease gene onto the damaged chromosome via homologous recombination (see, e.g., Burt & Koufopanou (2004) *Curr. Opin. Genet. Dev.*, 14:609-615). The copying process is termed 'homing', while the endonuclease-containing cassette that is copied is referred to as a "gene drive construct", a "gene drive", or simply a "drive". In sexually reproducing species, copying causes the fraction of offspring that inherit the cassette to be greater than ½, and these genes can therefore drive through a population even if they reduce the reproductive fitness of the individual organisms that carry them. Over many generations, this self-sustaining process can theoretically allow a gene drive to spread from a small number of individuals until it is present in all members of a population.

An engineered gene drive system can use a targeted endonuclease gene (e.g., a CRISPR/Cas construct) in place of a homing endonuclease gene. The endonuclease transgene is inserted in place of a natural sequence that it can cut. In typical embodiments, the endonuclease transgene construct is provided appropriate flanking homology sequences so that when the expressed endonuclease cleaves the corresponding site in an unmodified genome (e.g., genomic locus) a copy of the construct comprising the endonuclease transgene is inserted into the corresponding (previously unmodified) locus via homologous recombination. Most engineered gene-drive systems use CRISPR-Cas9 editing to duplicate a synthetic sequence from one modified chromosome to its wild-type counterpart during sexual reproduction. Importantly, current gene-drive strategies were understood to only work in sexually reproducing organisms such as animals and plants and it was believed they could not be applied to asexual populations such as viruses and bacteria.

However, described herein is a novel gene-drive system that allows the spreading of an engineered trait in populations of DNA viruses, and in particular herpesviruses. By way of illustration, Example 1 describes the successful transmission of a gene-drive sequence between distinct strains of cytomegalovirus (Human Herpesvirus 5). However, the methods described herein are believed to be generally applicable to essentially any DNA virus.

In certain embodiments the gene drive systems described herein can be used to stop or drastically circumvent the spreading of infectious viruses. Thus, for example, such a strategy could be used as a novel cure against any herpesviruses. The gene drive systems described herein additionally or alternatively be used to drive any desired transgene into a population to produce a modified viral population encoding that transgene.

In various illustrative embodiments, the methods of utilizing gene drive constructs in viral systems involves 1) transfecting or infecting cells with a modified DNA virus containing a gene drive construct; and infecting that cells with the target virus (virus to be modified) where the genome of the target DNA virus is modified by insertion of the gene drive construct into the genome of the target DNA virus and a population of modified target viruses is produced.

Where the modified virus containing the gene drive construct retains its ability to infect a cell, modified virus can be introduced into the cell by infection (using the virus's endogenous cell-entry machinery) or by transfection (e.g., by nucleofection, electroporation, etc.). Where the gene drive construct inhibits viral infectivity, the modified virus can be provided with a "rescue" gene to permit infectivity, or the modified virus can simply be transfected into the cell. In certain embodiments, where the modified virus contains a rescue gene that rescue gene can be under control of an inducible promoter and infectivity of the virus can be initiated/restored by providing the inducer for that promoter.

Figure 2:
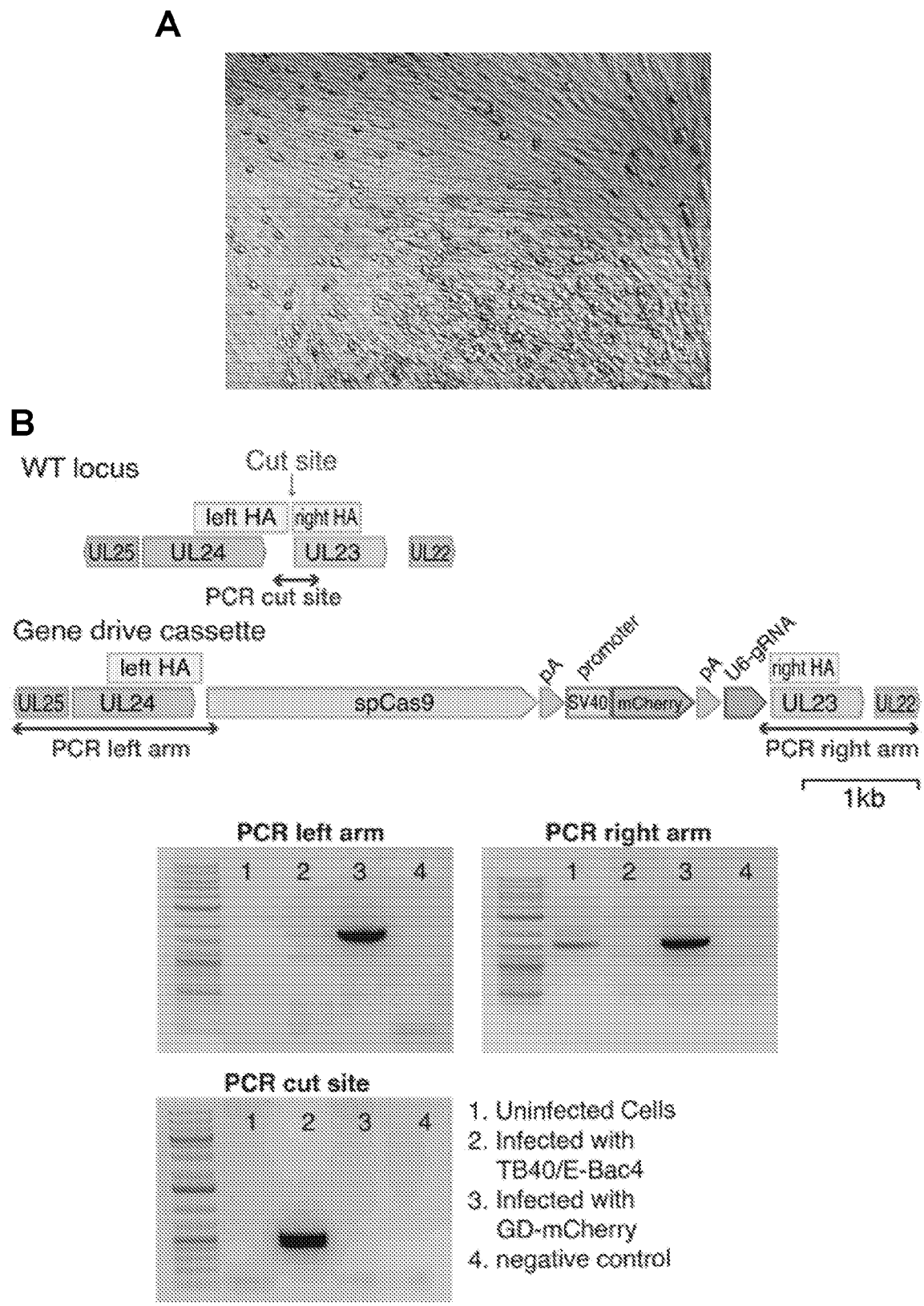
FIG. 2, panels A-C, illustrates the generation of gene drive viruses. Panel A) Image of a, mCherry-expressing viral plaque after transfection of fibroblasts with gene drive plasmid and infection with hCMV (TB40/E strain), around 10 days after infection. Panel B) Genotyping PCR of pure GD-mCherry population and primer localization. Panel C) Close-up on UL23 CRISPR cut site and sequence of WT (SEQ ID NO:1) and modified (SEQ ID NO:2) viruses.

One illustrative, but non-limiting gene drive construct for use in the methods described is shown in FIG. 2. As illustrated this gene drive construct comprises a targeted endonuclease (e.g., Cas9, TALEN, ZFP, etc.) operably linked to (under control of) a promoter). The construct is flanked by a left and a right homology arm to provide for insertion into a target site and the endonuclease is targeted (e.g., by TAL to cleave a target genome at a site corresponding to the location of the gene drive construct so that after cleavage a gene drive construct is inserted into the cleaved site. Where required by the targeted endonuclease, the construct typically encodes one or more guide RNAs, also operably linked to one or more promoters. In certain embodiments the construct can (optionally) additionally include one or more genes (cDNAs) to be expressed. In certain embodiments, where the construct inhibits/disrupts a gene, the gene/CDNA insert can be a rescue for the knockout. Alternatively, the gene/cDNA can express a detectable marker or can encode another protein that is to be expressed by the target viral genome. Where the targeted endonuclease does not utilize a guide RNA, the nucleic acid encoding the gRNAs can be omitted. In certain embodiments where the targeted endonuclease utilizes a guide RNA (gRNA) multiple guide RNAs can be provided that target multiple sites. Targeting multiple sites increases the cutting frequency and hinders the evolution of drive resistant alleles.

In certain embodiments to treat a viral invention (e.g., to inhibit or stop a viral infection), the gene drive construct is designed to knock-out one or more essential viral genes. Thus, for example the construct can be designed to insert into a gene associated with viral infection, and/or a gene associated with viral replication. The genome of the modified viruses (now containing the gene drive construct) will lack an essential viral gene (replaced by the nucleic acid encoding the endonuclease (e.g., encoding Cas9 and gRNA(s)), thereby preventing the production of infectious virions. However, upon co-infection by a gene-drive and a wildtype virus, new infectious gene-drive virions can be produced using the gene products of the wildtype genome. Concomitantly, expression of the targeted endonuclease (e.g., Cas9) from the gene-drive genome would inactivate the wildtype virus and convert it into new gene-drive genome. In various embodiments this strategy relies on the dynamics of expression of the endonuclease (e.g., Cas9) from the gene drive genome, and the corresponding wildtype gene. In particular, enough wildtype protein should be produced from the wildtype genome before the endonuclease (e.g., Cas9) is expressed and inactivates it.

Target Viruses and Genes.

Without being bound to a particular theory, it is believed the methods described herein can be used with numerous DNA viruses. In certain embodiments preferred requirements for a viral gene drive are: 1) A dsDNA genome large enough to add the 6-7 kb gene drive sequence which, in certain embodiments represents a minimal viral genome size of ~50 kb; and 2) The capacity to undergo homologous recombination. This second condition can be satisfied by any nuclear-replicating virus, because these viruses use the cellular recombination machinery. Nuclear-replicating viruses represent the majority of dsDNA viruses. Some dsDNA viruses such as poxviruses replicate in the cytoplasm but could still be potential gene drive targets as it has been shown that they often encode their own DNA repair machinery and can undergo homologous recombination in the cytoplasm.

Illustrative suitable DNA viruses include but are not limited to members of the order Herpesvirales (e.g., family Alloherpesviridae, and Herpesviridae) and the order Ligamenvirales (e.g., family Lipothrixviridae and Rudiviridae).

In certain embodiments the DNA virus comprise a virus selected from one of the following DNA virus families: Herpesviridae, Alloherpesviridae, Malacoherpesviridae, Lipothrixviridae, Rudiviridae, Adenoviridae, Ampullaviridae, Ascoviridae, Asfarviridae, Baculoviridae, Bicaudaviridae, Clavaviridae, Corticoviridae, Fuselloviridae, Globuloviridae, Guttaviridae, Hytrosaviridae, Iridoviridae, Lavidaviridae, Marseilleviridae, Mimiviridae, Nudiviridae, Nimaviridae, Pandoraviridae, Papillomaviridae, Phycodnaviridae, Plasmaviridae, Polydnaviruses, Polyomaviridae, Poxviridae, Sphaerolipoviridae, Tectiviridae, and Turriviridae.

In certain embodiments the DNA virus comprises a member of the Herpesviridae. Illustrative human herpes viruses are identified below in Table 1.

TABLE 1

Illustrative herpes viruses known to cause disease in humans.

| Name | Synonym | Pathophysiology |
|---|---|---|
| HHV-1 | Herpes simplex virus-1 (HSV-1) | Oral and/or genital herpes (predominantly orofacial), as well as other herpes simplex infections |
| HHV-2 | Herpes simplex virus-2 (HSV-2) | Oral and/or genital herpes (predominantly genital), as well as other herpes simplex infections |
| HHV-3 | Varicella zoster virus (VZV) | Chickenpox and shingles |
| HHV-4 | Epstein-Barr virus (EBV), lymphocryptovirus | Infectious mononucleosis, Burkitt's lymphoma, CNS lymphoma in AIDS patients, post-transplant lymphoproliferative syndrome (PTLD), nasopharyngeal carcinoma, HIV-associated hairy leukoplakia |
| HHV-5 | Cytomegalovirus (CMV) | Infectious mononucleosis-like syndrome,[21] retinitis |
| HHV-6A and 6B | Roseolovirus, Herpes lymphotropic virus | Sixth disease (roseola infantum or exanthem subitum) |
| HHV-7 | | Drug-induced hypersensitivity syndrome, encephalopathy, hemiconvulsion-hemiplegia-epilepsy syndrome, hepatitis infection, postinfectious myeloradiculoneuropathy, pityriasis rosea, and the reactivation of HHV-4, leading to "mononucleosis-like illness" |
| HHV-8 | Kaposi's sarcoma-associated herpesvirus (KSHV) | Kaposi's sarcoma, primary effusion lymphoma, some types of multicentric Castleman's disease |

In certain embodiments zoonotic herpesvirus (viruses associated primarily with animals but that may infect humans) are also contemplated for use with gene drive constructs as described herein. Such zoonotic herpesviruses include but are not limited to CeHV-1 (monkey B virus that can infect humans), MuHV-4 (Murid herpesvirus 68, infect 4.5% of the human population), and the like. In certain embodiments animal herpesviruses that are potentially important for the farming industry and for environmental control, are of particular importance. Such animal herpesviruses include, but are not limited to SuHV1 (Aujeszky's disease in pigs and other animals), BoHV-1 in cattle (*Gallid herpesvirus* 1), GalHV-1 in chicken, and MDV (Marek's disease virus which infects chickens).

Other suitable viruses include, but are not limited to Adenoviruses (any virus of the family Adenoviridae), Baculoviruses (any virus of the family Baculoviridae), Nucleocytoplasmic large DNA viruses, such as viruses of the families Ascoviridae, and Asfarviridae (include African swine fever virus, that cause a hemorrhagic fever with high mortality rates in pigs), Poxviridae (include smallpox), Iridoviridae, Marseilleviridae, Megaviridae, Pandoraviridae, Phycodnaviridae, Pithoviridae, and the like.

The genomes of the DNA viruses are well characterized (see, e.g., McGeoch et al. (1988) *J Gen. Virol.* 69: 1531-1574; Baradaran et al. (1994) *J Virol.* 68: 4251-4261; Barker & Roizman (1992) *J Virol.* 66: 562-566; Carter & Roizman (1996) *J Virol.* 70: 172-178; Cho & Roizman (1986) *J Virol.* 57: 629-637; Georgopoulou et al. (1993) *J Virol.* 67: 3961-3968; Lagunoff & Roizman (1994) *J Virol.* 68: 6021-6028; Liu & Roizman (1991) *J Virol.* 65: 206-212; Ward et al. (1996) *J. Virol.* 70: 2684-2690; Martinez et al. (1996) *Virology,* 215 152-164; and the like) and, in view of the teachings provided herein, particular genes suitable for targeting using the gene drive constructs described herein will be recognized by one of skill in the art. 01791 By way of illustration, a list of known herpes simplex genes is shown in Table 2. In certain embodiments the gene drive constructs can be targeted to any one or more of the genes shown in Table 2, or to orthologs or homologs thereof.

TABLE 2

Illustrative, but non-limiting list of herpes simplex viral genes.

| Gene | Product | Function of gene product |
|---|---|---|
| $\gamma_1 34.5$ | ICP34.5 | Null mutants are attenuated and fail to block phosphorylation of eIF-2α by activated protein kinase RNA-dependent kinase; carboxyl terminus homologous to the corresponding domain of the GADD34 proteins. |
| ORF-P | ORF-P | ORF is antisense to the $\gamma_1 34.5$ gene and repressed by binding of ICP4 to cap site. Proteins interact with p32, a component of SF2/ASF splicing factor. |
| ORF-O | ORF-O | Overlaps with ORF P, a protein made by frameshift from ORF-P. |
| $\alpha_0$ | ICP0 | Promiscuous transactivator, requires ICP4 for optimal activity; nucleotidylylated, phosphorylated by $U_L 13$, nuclear (early) and cytoplasmic (late) phases. Null mutants debilitated at low multiplicities of infection. |
| $U_L 1$ | gL | Complex with gH required for transport of both proteins to plasma membrane and for viral entry mediated by gH. |

TABLE 2-continued

Illustrative, but non-limiting list of herpes simplex viral genes.

| Gene | Product | Function of gene product |
|---|---|---|
| $U_L2$ | | Uracil DNA glycosylase. |
| $U_L3$ | | Nuclear phosphoprotein of unknown function. Reported to localize to perinuclear region early and to the nucleus late in infection. |
| $U_L4$ | | Unknown. |
| $U_L5$ | | Forms complex with $U_L8$ and $U_L52$ proteins. |
| $U_L6$ | | Virion protein; required for DNA cleavage and packaging. |
| $U_L7$ | | Unknown. |
| $U_L8$ | | Forms complex with $U_L5$ and $U_L52$ (helicase/primase complex). Stabilizes interaction between primers and DNA template. |
| $U_L9$ | | Binds to origins of DNA synthesis in sequence-specific (origin) fashion; carries out helicase and ATPase activities. |
| $U_L10$ | gM | Glycoprotein present in virions and plasma membranes. |
| $U_L10.5$ | | Unknown. |
| $U_L11$ | | Myristoylated protein; necessary for efficient capsid envelopment and exocytosis. |
| $U_L12$ | | Exonuclease (DNase) involved in viral nucleic acid metabolism; reported to localize in nucleoli and in virally induced nuclear dense bodies and to bind α sequence along with other unidentified proteins. Complex may be involved in cleavage/packaging of viral DNA. |
| $U_L12.5$ | | Nuclease-associated with capsids. |
| $U_L13$ | | Virion (nuclear) protein kinase; substrates include ICP0, ICP22, vhs, $U_L3$, $U_L49$, etc. |
| $U_L14$ | | Unknown. |
| $U_L15$ | | ts mutant DNA+. Two exons; protein required for cleavage/packaging of DNA. |
| $U_L16$ | | Virion protein; gene located within intron of $U_L15$. |
| $U_L17$ | | Located within intron of $U_L15$. |
| $U_L18$ | VP23 | Protein required for capsid formation and cleavage/packaging of DNA. |
| $U_L19$ | VP5, ICP5 | Major capsid protein. |
| $U_L20$ | | Membrane protein, associates with nuclear membranes, Golgi stacks, etc. Essential for viral exocytosis. |
| $U_L20.5$ | | Unknown. |
| $U_L21$ | | Nucleotidylylated phosphoprotein; unknown function. |
| $U_L22$ | gH | Forms complex with gL (see above). Required for entry, egress, and cell-cell spread. |
| $U_L23$ | ICP36 | Thymidine (nucleoside) kinase. |
| $U_L24$ | | Syn⁻ locus; membrane-associated protein? |
| $U_L25$ | | Virion protein reported to be required for packaging of cleaved viral DNA. |
| $U_L26$ | | Serine protease; substrates are $U_L26$ protein and $U_L26.5$ (IC35). VP21 (C portion of $U_L26$), VP24 (N terminus of protease) are products of the self-cleavage of $U_L26$. |
| $U_L26.5$ | ICP35 | Substrate of $U_L26$ protease unique to B capsids and forms inner core or scaffolding; the precursor, ICP35b,c is cleaved to e, f. On packaging of DNA it is removed from capsid shell. |
| $U_L27$ | gB, VP7 | Glycoprotein required for viral entry; forms a dimer and induces neutralizing antibody. A syn⁻ locus maps to the carboxyl terminus. |
| $U_L27.5$ | | Unknown, antisense to gB. |
| $U_L28$ | ICP18.5 | $M_r$ 87-95 K protein required for DNA cleavage/packaging. |
| $U_L29$ | ICP8 | Binds single-stranded DNA cooperatively, required for viral DNA replication: forms complex with DNA polymerase and $U_L42$. ts mutants are DNA⁻ and hence expression of early and late genes may be affected positively or negatively by ICP8. Because ICP8 denatures DNA, it affects renaturation of complementary strands of DNA and affects homologous pairing and strand transfer. |
| $U_L30$ | | DNA polymerase; forms complex with ICP8 and C terminal 247 amino acids of $U_L42$. |
| $U_L31$ | | Nucleotidylylated phosphoprotein, cofractionates with nuclear matrix. |
| $U_L32$ | | Cytoplasmic/nuclear protein required for DNA cleavage/packaging. |
| $U_L33$ | | DNA packaging; necessary for assembly of capsids containing DNA. |
| $U_L34$ | | Abundant nonglycosylated, membrane-associated, virion protein phosphorylated by $U_S3$. |
| $U_L35$ | VP26 | Basic phosphorylated capsid protein. |
| $U_L36$ | ICP1-2 | Tegument phosphoprotein. DNA is not released from capsids at nuclear pores in cells infected with tsmutant. Reported to form complex with a $M_r$ 140 K protein that binds α sequence DNA. |

TABLE 2-continued

Illustrative, but non-limiting list of herpes simplex viral genes.

| Gene | Product | Function of gene product |
|---|---|---|
| $U_L37$ | ICP32 | Cytoplasmic phosphoprotein; in presence of ICP8 it is transported to nucleus and associates with DNA, but phosphorylation is not dependent on ICP8. Required for maturation of virions. |
| $U_L38$ | VP19C | Capsid assembly protein, binds DNA and may be involved in anchoring DNA in the capsid. |
| $U_L39$ | ICP6 | Large subunit of ribonucleotide reductase. Autophosphorylates via unique N terminus but does not trans-phosphorylate. |
| $U_L40$ | | Small subunit of ribonucleotide reductase. |
| $U_L41$ | VHS | Causes nonspecific degradation of mRNA after infection; shuts off host protein synthesis, enables sequential synthesis of viral proteins. |
| $U_L42$ | | Double-stranded DNA-binding protein, binds to and increases processivity of DNA polymerase. |
| $U_L43$ | | Amino acid sequence predicts membrane-associated protein. |
| $U_L43.5$ | | Antisense to $U_L43$; low abundance nuclear protein; accumulates in assemblons. |
| $U_L44$ | gC, VP7.5 | Glycoprotein involved in cell attachment; required for attachment to the apical surface of polarized MDCK cells. |
| $U_L45$ | | Encodes a $M_r$ 18 K protein of unknown function. |
| $U_L46$ | VP11/12 | Tegument phosphoprotein reported to modulate the activity of $U_L48$ (αTIF). |
| $U_L47$ | VP13/14 | Nucleotidylylated tegument phosphoprotein modulates the activity of UL48 (αTIF). |
| $U_L48$ | VP16, ICP25, αTIF | Tegument protein, induces a genes by interacting with OctI. The complex binds to specific sequences with the consensus GyATGnTAATGArATTCyTTGnGGG-NC. |
| $U_L49$ | VP22 | Nucleotidylylated, mono(ADP-ribosyl)ated tegument phosphoprotein. |
| $U_L49.5$ | | Sequence predicts a $M_r$ 12,000 membrane-associated protein. |
| $U_L50$ | | dUTPase. |
| $U_L51$ | | Unknown. |
| $U_L52$ | | Component of the helicase/primase complex. |
| $U_L53$ | gK | Glycoprotein required for efficient viral exocytosis; contains syn⁻ locus. |
| α27 | ICP27 | Nucleotidylylated multifunctional regulatory protein; causes redistribution of snRNPs, inhibits RNA splicing. It is required for late gene expression, and negatively regulates early genes. |
| $U_L55$ | | Unknown. |
| $U_L56$ | | Nuclear, virion-associated protein of unknown function. |
| α4 | ICP4 | Nucleotidylylated, poly(ADP-ribosyl)ated phosphoprotein; regulates positively most β and γ genes and negatively itself, ORF-P and the a0 gene; blocks apoptosis. Binds to DNA in sequence specific fashion. |
| α22 | ICP22 | Nucleotidylylated regulatory protein, phosphorylated by $U_L13$ and $U_S3$ protein kinases, required for optimal expression of ICP0 and of a subset of γ proteins. |
| $U_S1.5$ | $U_S1.5$ | Regulatory protein; extent to which it shares function with ICP22 not known. |
| $U_S2$ | | Unknown. |
| $U_S3$ | | Protein kinase; major substrate is $U_L34$ protein. |
| $U_S4$ | gG | Glycoprotein involved in entry, egress, and spread from cell to cell. |
| $U_S5$ | gJ(?) | Sequence predicts glycoprotein. |
| $U_S6$ | gD | |
| VP17/18 | | Glycoprotein required for post-attachment entry of virus into cells. |
| $U_S7$ | gI | gI and gE glycoproteins form complex for transport to plasma membrane and also to constitute a high-affinity Fc receptor. gI is required for basolateral spread of virus in polarized cells. |
| $U_S8$ | gE | FC receptor; involved in basolateral spread of virus in polarized cells. |
| $U_S8.5$ | | Unknown. |
| $U_S9$ | | Tegument protein phosphorylated by $U_L13$. |
| $U_S10$ | | Tegument protein. |
| $U_S11$ | | Tegument protein binds to $U_L34$ mRNA in sequence- and conformation-specific fashion; binds to the 60S ribosomal subunit and localizes in the nucleolus. |
| α47 | ICP47 | Binds to TAP1/TAP2 and to block antigen presentation to CD8⁺ cells. |
| $Ori_STU$ | $Ori_SRNA$ | RNA transcribed across S origins of DNA synthesis. Function is not known. |
| LATU | LATs | Transcripts, found in latently infected neurons. Function is not known. |

By way of illustration, a list of HHV-5 and HHV-6 genes is shown in Table 3. In certain embodiments the gene drive constructs can be targeted to any one or more of the genes shown in Table 3, or to orthologs or homologs thereof.

TABLE 3

Illustrative, but non-limiting list of HHV-5 and HHV-6 viral genes that can be used as targets for gene drive disruption.

| HHV-6 ORF | HHV-5 (hCMV) ORF | Function of gene product |
|---|---|---|
| DR1 | | US22 |
| DR6 | | US22, transactivator, putative oncogene |
| DR7/U1 | | SR domain, malignant transforming activity, binds to p53 |
| U2 | UL23 | CMV US22 gene family, |
| U3 | UL24 | CMV US22 gene family, transactivator |
| U4 | UL27 | CMV Maribavir resistance |
| U7 | UL28 | CMV US22 gene family |
| U10 | | dUTPase family |
| U11 | UL32 | Antigenic tegument protein |
| U12 | UL33 | Chemokine G protein-coupled receptor |
| U13 | UL34 | CMV: Represses US3 transcription |
| U14 | UL25 | CMV UL25 gene family, antigenic tegument protein, binds p53 |
| U15 | | CMV UL25 gene family |
| U17 | UL36 | CMV US22 gene family, tegument protein |
| U18 | UL37EX3 | IE-B membrane glycoprotein |
| U19 | UL38 | IE-B protein, glycoprotein |
| U20 | Glycoprotein | Specific to HHV-6/7, Glycoprotein, immunoglobulin structure |
| U21 | Glycoprotein | Glycoprotein, downregulates HLA I, specific to HHV-6/7 |
| U22 | Glycoprotein | Glycoprotein, specific to HHV-6 |
| U23 | Glycoprotein | Glycoprotein, specific to HHV-6 |
| U24 | Glycoprotein | Glycoprotein |
| U25 | UL43 | CMV UL22 gene family, tegument protein |
| U26 | Putative | Putative multiple transmembrane protein |
| U27 | UL44 | DNA polymerase processivity factor |
| U28 | UL45 | Ribonucleotide reducactase large subunit, tegument protein |
| U29 | UL46 | Capsid asembly and DNA maturation |
| U30 | UL47 | Tegument protein |
| U31 | UL48 | Large tegument protein |
| U32 | UL48a | Capsid protein, hexon tips |
| U33 | UL49 | Virion protein |
| U34 | UL50 | Membrane-associated phosphoprotein, |
| U35 | UL51 | DNA packaging, terminase component, |
| U36 | UL52 | DNA packaging |
| U37 | UL53 | Primary envelopment, phosphoprotein |
| U38 | UL54 | DNA polymerase |
| U39 | UL55 | Glycoprotein B (gB) |
| U40 | UL56 | Transport/capsid assembly (TP) |
| U41 | UL57 | Major DNA binding protein (MDBP) |
| U42 | UL69 | Tegument protein, cell cycle block, transactivator |
| U43 | UL70 | DNA helicase/primase complex |
| U44 | UL71 | Tegument protein |
| U45 | UL72 | dUTPase |
| U46 | UL73 | Membrane protein |
| U47 | UL74 | Glycoprotein O (gO) |
| U48 | UL75 | Glycoprotein H (gH) |
| U49 | UL76 | Putative fusion protein |
| U50 | UL77 | DNA packaging |
| U51 | UL78 | G-protein-coupled receptor |
| U52 | UL79 | |
| U53 | UL80 | Protease, capsid assembly protein |
| U54 | UL82/UL83 | Tegument protein, Virion transactivator |
| U55 | UL84 | Role in DNA synthesis, dUTPase |
| U56 | UL85 | Capsid protein |
| U57 | UL86 | Major capsid protein (MCP) |
| U58 | UL87 | |
| U59 | UL88 | Tegument protein |
| U61 | | |
| U62 | UL91 | |
| U63 | UL92 | |
| U64 | UL93 | DNA packaging; tegument protein |
| U65 | UL94 | Tegument protein |
| U66 | UL89 | Terminase component |
| U69 | UL97 | Phosphotransferase, Ganciclovir kinase |
| U70 | UL98 | Alkaline exonuclease (Exo) |
| U71 | UL99 | Myristylated virion protein |
| U72 | UL100 | Glycoprotein M (gM) |
| U73 | Origin | Origin-binding protein (OBP) |
| U74 | UL102 | DNA Helicase-primase complex (HP) |

TABLE 3-continued

Illustrative, but non-limiting list of HHV-5 and HHV-6 viral genes that can be used as targets for gene drive disruption.

| HHV-6 ORF | HHV-5 (hCMV) ORF | Function of gene product |
|---|---|---|
| U75 | UL103 | Tegument protein |
| U76 | UL104 | DNA packaging, virion protein |
| U77 | UL105 | Helicase-primase complex (HP) |
| U79 | UL112/UL113 | Transcriptional activation |
| U81 | UL114 | Uracil-DNA glycosylase |
| U82 | UL115 | Glycoprotein L (gL) |
| U83 | Secreted | Secreted glycoprotein, CC chemokine |
| U85 | UL119 | Glycoprotein |
| U86 | UL122 | IE-A |
| U88 | IE-A | IE-A |
| U90 | UL123 | IE-A (IE 1), transactivator |
| U91 | UL124 | IE-A |
| U94 | | Parvovirus rep homolog (Rep) |
| U95 | | CMV US22 gene family |
| U100 | | Spliced envelope glycoprotein Q, assoc. with lipid rafts |

In certain embodiments the gene drive construct can be targeted to UL79, e.g, as illustrated in Example 1. In certain embodiments the gene drive construct can be targeted to one or more of, UL122 (immediate-early expression), UL79 (early-late expression), UL99, UL23 and UL55 or to homologs or orthologs thereof.

Illustrative gene targets and corresponding illustrative gRNA sequences are shown in Table 4

TABLE 4

Illustrative gene targets in hCMV and illustrative gRNA sequences.

| Gene Name | gRNA Sequences | SEQ ID NO |
|---|---|---|
| UL79 | TAGATGATTGGCGCAAGTAA, | 6 |
| | ATTAGCGAGAAGATGTCGCG | 7 |
| UL122 | TTGGAGGAAGGGCCCTCGTC, | 8 |
| | ATCAGGGTCCATCTTTCTCT | 9 |
| UL99 | GCGACCCAGAGCATCTTTCA, | 10 |
| | CCGACTTCCTCCTCGGACGA | 11 |
| UL55 | GGACGACCTCATGAGCGGCC, | 12 |
| | AAGGCCGTTGGCGTAGCCAT | 13 |
| UL23 | ACATCGCGGTCGCGCGTCGG, | 14 |
| | GTCCTTGATTACCGACATCG, | 15 |
| | TCAATCTGCTCGACCGCTGG, | 16 |
| | TTCTCAATCTGCTCGACCGC | 17 |
| UL75 | CAAAAAGACATCGAGGCATA | 18 |
| UL92 | | |
| UL44 | | |
| UL82 | | |

It will be recognized that the above-identified DNA viruses and gene are illustrative and not limiting. Using the teachings provided herein gene drive constructs for use in the other viruses and/or targeting other genes will be available to one of skill in the art.

Cells Used for the Methods.

In various embodiments the methods described herein involve transfecting or infecting a cell (or cell population) with a modified DNA virus containing a gene drive construct (e.g., as described herein, and infecting cells with the target virus where the genome of the target DNA virus is modified by insertion of the gene drive construct into the genome of the target DNA virus and a population of modified target viruses (containing the gene drive construct) is produced.

In various embodiments the cell into which the modified DNA virus and the target DNA virus is introduced can be any cell convenient for such a purpose. In certain embodiments the cell is a cell characteristic of an organism that the virus is known to infect. In certain embodiments the cell is a eukaryotic cell, especially a vertebrate cell. In certain embodiments the cell is a mammalian cell and, in particular embodiments a human cell. It will be recognized that in certain embodiments veterinary and other applications are contemplated and in such instances the cell may be a non-human mammalian cell.

In certain embodiments the cells are acutely derived cells, while in other embodiments the cells are cells of a cell line. By way of illustration in certain embodiments the cells are fibroblasts (e.g., human foreskin fibroblasts (HFF)) as illustrated in Example 1. This example is illustrative and non-limiting and essentially any other cell that the virus of interest can infect and propagate in can be utilized.

In this respect, it is noted that herpes simplex viruses (HSV) are part of the alphaherpesvirus subfamily of herpesviruses. There are two types of HSV: type-1 (HSV-1) and type-2 (HSV-2). These viruses are neurotropic capable of infecting the nervous system and causing neurological diseases. Moreover, unlike many herpesviruses, HSV has low species specificity and a wide host range. It has the unparalleled ability to infect human and nonhuman cells alike (see, e.g., Spear & Longnecker (2003) *J Virol.* 77(19): 10179-10185). Illustrative cell lines known to be infected by HSF include, but are not limited to primary human trabecular meshwork (HSV-1), primary human corneal fibroblasts (HSV-1), primary human corneal fibroblasts (HSV-2), human conjunctival epithelium (HSV-1), retinal pigment epithelium (HSV-1), human corneal epithelium (HSV-1), retinal pigment epithelium (HSV-2), radial glial cells and Cajal-Retzius cells, soma and processes of central and peripheral neurons, ependymal cells, choroid plexus epithelium, vascular endothelium, meningothelial cells (HSV-1, HSV-2), human Mesenchymal Stem Cells (HSV-1), and the like.

In certain embodiments the modified DNA virus (containing gene drive construct) and the target virus (e.g., wildtype virus) are introduced into a cell ex vivo. In certain embodiments the cell is maintained in a cell culture.

However, in certain embodiments, the modified DNA virus (containing gene drive construct) and the target virus (e.g., wildtype virus) are introduced into a cell in vivo. In certain embodiments the cell can be a cell, e.g., in a mammal, that is already infected with the target virus (virus to be modified). Thus, for example, where the mammal is infected with a wild type virus, the gene drive virus can be introduced into the subject, e.g., by infection where the gene drive virus retains infectivity (or has infectivity temporarily restored by, e.g., an inducible or transitional rescue gene). In certain embodiments the gene drive virus can be introduced into cells of the subject by other means (e.g., encapsulated in delivery vehicles, complexed with dendrimers or polymeric delivery particles, and the like).

Targeted Endonucleases.

The gene drive constructs used in the methods described herein comprise, inter alia, a nucleic acid encoding a targeted endonuclease. In certain embodiments the encoded targeted endonuclease is a naturally occurring endonuclease (e.g., a site-specific "homing" endonuclease. In certain embodiments the targeted endonuclease include but are not limited to, CRISPR/cas endonucleases, zinc finger endonucleases, Transcription Activator-Like Effector Nuclease(s) (TALENs), and the like.

CRISPR/Cas Systems

In certain embodiments the targeted endonuclease can comprise a CRISPR/Cas endonuclease that is typically guided to a target site by one or more guide RNAs (gRNAs). CRISPR-based endonucleases are RNA-guided endonucleases derived from CRISPR/Cas systems. Bacteria and archaea have evolved an RNA-based adaptive immune system that uses CRISPR (clustered regularly interspersed short palindromic repeat) and Cas (CRISPR-associated) proteins to detect and destroy invading viruses or plasmids. CRISPR/Cas endonucleases can be programmed to introduce targeted site-specific double-strand breaks by providing target-specific synthetic guide RNAs (see, e.g., Jinek et al. (2012) *Science,* 337: 816-821).

In various embodiments the CRISPR-based endonuclease can be derived from a CRISPR/Cas type I, type II, type III, type V, or type VI system. Non-limiting examples of suitable CRISPR/Cas proteins include Cas3, Cas4, Cas5, Cas5e (or CasD), Cas6, Cas6e, Cas6f, Cas7, Cas8a1, Cas8a2, Cas8b, Cas8c, Cas9, Cas10, Cas10d, CasF, CasG, CasH, Csy1, Csy2, Csy3, Cse1 (or CasA), Cse2 (or CasB), Cse3 (or CasE), Cse4 (or CasC), Csc1, Csc2, Csa5, Csn2, Csm2, Csm3, Csm4, Csm5, Csm6, Cmra, Cmr3, Cmr4, Cmr5, Cmr6, Csb1, Csb2, Csb3, Csx17, Csx14, Csx10, Csx16, CsaX, Csx3, Csz1, Csx15, Csf1, Csf2, Csf3, Csf4, Cul966, and the like.

Type II CRISPR/Cas Endonucleases (e.g., Cas 9)

In certain embodiments, the CRISPR-based endonuclease is derived from a type II CRISPR/Cas system. In illustrative, but non-limiting embodiments, the CRISPR-based endonuclease is derived from a Cas9 protein. In certain embodiments the Cas9 protein can be from *Streptococcus pyogenes, Streptococcus thermophilus, Streptococcus* sp., *Nocardiopsis dassonvillei, Streptomyces pristinaespiralis, Streptomyces viridochromogenes, Streptomyces viridochromogenes, Streptosporangium roseum, Streptosporangium roseum, Alicyclobacillus acidocaldarius, Bacillus pseudomycoides, Bacillus selenitireducens, Exiguobacterium sibiricum, Lactobacillus delbrueckii, Lactobacillus salivarius, Microscilla marina, Burkholderiales bacterium, Polaromonas naphthalenivorans, Polaromonas* sp., *Crocosphaera watsonii, Cyanothece* sp., *Microcystis aeruginosa, Synechococcus* sp., *Acetohalobium arabaticum, Ammonifex degensii, Caldicelulosiruptor becscii, Candidatus Desulforudis, Clostridium botulinum, Clostridium difficile, Finegoldia magna, Natranaerobius thermophilus, Pelotomaculum thermopropionicum, Acidithiobacillus caldus, Acidithiobacillus ferrooxidans, Allochromatium vinosum, Marinobacter* sp., *Nitrosococcus halophilus, Nitrosococcus watsoni, Pseudoalteromonas haloplanktis, Ktedonobacter racemifer, Methanohalobium evestigatum, Anabaena variabilis, Nodularia spumigena, Nostoc* sp., *Arthrospira maxima, Arthrospira platensis, Arthrospira* sp., *Lyngbya* sp., *Microcoleus chthonoplastes, Oscillatoria* sp., *Petrotoga mobilis, Thermosipho africanus*, or *Acaryochloris marina*. In one specific illustrative embodiment, the CRISPR-based nuclease is derived from a Cas9 protein from *Streptococcus pyogenes.*

In general, CRISPR/Cas proteins comprise at least one RNA recognition and/or RNA binding domain. RNA recognition and/or RNA binding domains interact with the guide RNA such that the CRISPR/Cas protein is directed to a specific genomic or genomic sequence. CRISPR/Cas proteins can also comprise nuclease domains (i.e., DNase or RNase domains), DNA binding domains, helicase domains, protein-protein interaction domains, dimerization domains, as well as other domains.

In certain embodiments the CRISPR-based endonuclease used in the constructs and methods described herein can be a wild type CRISPR/Cas protein, a modified CRISPR/Cas protein, or a fragment of a wild type or modified CRISPR/Cas protein. In certain embodiments the CRISPR/Cas protein can be modified to increase nucleic acid binding affinity and/or specificity, alter an enzymatic activity, and/or change another property of the protein. For example, the CRISPR/Cas protein can be truncated to remove domains that are not essential for the function of the protein. The CRISPR/Cas protein also can be truncated or modified to optimize the activity of the protein or an effector domain fused with the CRISPR/Cas protein.

In some embodiments, the CRISPR-based endonuclease can be derived from a wild type Cas9 protein, modified forms, or fragment thereof. In other embodiments, the CRISPR-based endonuclease can be derived from a modified Cas9 protein. For example, the amino acid sequence of the Cas9 protein can be modified to alter one or more properties (e.g., nuclease activity, affinity, stability, etc.) of the protein. Alternatively, domains of the Cas9 protein not involved in RNA-guided cleavage can be eliminated from the protein such that the modified Cas9 protein is smaller than the wild type Cas9 protein.

In general, a Cas9 protein comprises at least two nuclease (i.e., DNase) domains. For example, a Cas9 protein can comprise a RuvC-like nuclease domain and a HNH-like nuclease domain. The RuvC and HNH domains work together to cut single strands to make a double-strand break in DNA (see, e.g., Jinek et al. (2012) *Science,* 337: 816-821). In one embodiment, the CRISPR-based endonuclease is derived from a Cas9 protein and comprises two function nuclease domains, which together introduce a double-stranded break into the targeted site.

The target sites recognized by naturally occurring CRISPR/Cas systems typically having lengths of about 14-15 bp (see, e.g., Cong et al. (2013) *Science,* 339: 819-823). The target site has no sequence limitation except that sequence complementary to the 5' end of the guide RNA (i.e., called a protospacer sequence) is typically immediately followed by (3' or downstream) a consensus sequence. This consensus sequence is also known as a protospacer adjacent motif (or PAM). Examples of PAM include, but are not limited to, NGG, NGGNG, and NNAGAAW (wherein N is defined as any nucleotide and W is defined as either A or T). At the typical length, only about 5-7% of the target sites would be unique within a target genome, indicating that off target effects could be significant. The length of the target site can be expanded by requiring two binding events. For example, CRISPR-based endonucleases can be modified such that they can only cleave one strand of a double-stranded sequence (i.e., converted to nickases). Thus, the use of a CRISPR-based nickase in combination with two different guide RNAs would essentially double the length of the target site, while still effecting a double stranded break.

The requirement of the crRNA-tracrRNA complex in a CRISPR/Cas system can be avoided by use of an engineered "single-guide RNA" (sgRNA) that comprises the hairpin normally formed by the annealing of the crRNA and the tracrRNA (see Jinek et al. (2012) *Science* 337:816; Cong et al. (2013) *Sciencexpress* 10.1126/science.1231143). In *S. pyogenes*, the engineered tracrRNA:crRNA fusion, or the sgRNA, guides Cas9 to cleave the target DNA when a double strand RNA:DNA heterodimer forms between the Cas associated RNAs and the target DNA. This system comprising the Cas9 protein and an engineered sgRNA containing a PAM sequence has been used for RNA guided genome editing and has been useful for zebrafish embryo genomic editing in vivo (see Hwang et al. (2013) *Nat. Biotechnol.*, 31(3):227) with editing efficiencies similar to ZFNs and TALENs.

Accordingly in certain embodiments, a CRISPR/Cas endonuclease complex used in the constructs and methods described herein comprises a Cas protein and at least one to two ribonucleic acids (e.g., gRNAs) that are capable of directing the Cas protein to and hybridizing to a target motif of a target polynucleotide sequence. In some embodiments, a CRISPR/Cas endonuclease complex used in the methods described herein comprises a Cas protein and one ribonucleic acid (e.g., gRNA) that is capable of directing the Cas protein to and hybridizing to a target motif of a target polynucleotide sequence.

In some embodiments, a Cas protein comprises a core Cas protein. Illustrative Cas core proteins include, but are not limited to, Cas1, Cas2, Cas3, Cas4, Cas5, Cas6, Cas7, Cas8 and Cas9. In some embodiments, a Cas protein comprises a Cas protein of an *E. coli* subtype (also known as CASS2). Illustrative Cas proteins of the *E. Coli* subtype include, but are not limited to Cse1, Cse2, Cse3, Cse4, and Cas5e. In some embodiments, a Cas protein comprises a Cas protein of the Ypest subtype (also known as CASS3). Illustrative Cas proteins of the Ypest subtype include, but are not limited to Csy 1, Csy2, Csy3, and Csy4. In some embodiments, a Cas protein comprises a Cas protein of the Nmeni subtype (also known as CASS4). Illustrative Cas proteins of the Nmeni subtype include but are not limited to Csn1 and Csn2. In some embodiments, a Cas protein comprises a Cas protein of the Dvulg subtype (also known as CASS1). Illustrative Cas proteins of the Dvulg subtype include Csd1, Csd2, and Cas5d. In some embodiments, a Cas protein comprises a Cas protein of the Tneap subtype (also known as CASS7). Illustrative Cas proteins of the Tneap subtype include, but are not limited to, Cst1, Cst2, Cas5t. In some embodiments, a Cas protein comprises a Cas protein of the Hmari subtype. Illustrative Cas proteins of the Hmari subtype include, but are not limited to Csh1, Csh2, and Cas5h. In some embodiments, a Cas protein comprises a Cas protein of the Apem subtype (also known as CASS5). Illustrative Cas proteins of the Apem subtype include, but are not limited to Csa1, Csa2, Csa3, Csa4, Csa5, and Cas5a. In some embodiments, a Cas protein comprises a Cas protein of the Mtube subtype (also known as CASS6). Illustrative Cas proteins of the Mtube subtype include, but are not limited to Csm1, Csm2, Csm3, Csm4, and Csm5. In some embodiments, a Cas protein comprises a RAMP module Cas protein. Illustrative RAMP module Cas proteins include, but are not limited to, Cmr1, Cmr2, Cmr3, Cmr4, Cmr5, and Cmr6.

In some embodiments, the Cas protein is a *Streptococcus pyogenes* Cas9 protein (spCas9) or a functional portion thereof (see, e.g., UniProtKB-Q99ZW2 (CAS9_STRP1)). In some embodiments, the Cas protein is a *Staphylococcus aureus* Cas9 protein (saCas9) or a functional portion thereof. In some embodiments, the Cas protein is a *Streptococcus thermophilus* Cas9 protein (stCas9) or a functional portion thereof. In some embodiments, the Cas protein is a *Neisseria meningitides* Cas9 protein (nmCas9) or a functional portion thereof. In some embodiments, the Cas protein is a *Treponema denticola* Cas9 protein (tdCas9) or a functional portion thereof. In some embodiments, the Cas protein is Cas9 protein from any other bacterial species or functional portion thereof.

In certain embodiments the case 9 is mutated in one or more residues involved in the formation of non-specific DNA interactions. In certain embodiments such a Cas 9 comprises a mutated Cas9 such as eSpCas9 (see, e.g., Slaymaker, et al. (2016) *Science* 351: 84-88), SpCas9-HF1 (see, e.g., Kleinstiver et al. (2016) *Nature*, 529: 490-495), HypaCas9 (see, e.g., Chen et al. (2017) *Nature* 550: 407-410), and the like.

Type V and Type VI CRISPR/Cas Endonucleases

In certain embodiments the CRISPR/Cas endonuclease systems used in the constructs and methods contemplated herein include, but are not limited to a type V or type VI CRISPR/Cas endonuclease (e.g., the genome editing endonuclease is a type V or type VI CRISPR/Cas endonuclease) (e.g., Cpf1, C2c1, C2c2, C2c3). Type V and type VI CRISPR/Cas endonucleases are a type of class 2 CRISPR/Cas endonuclease. Examples of type V CRISPR/Cas endonucleases include but are not limited to: Cpf1, C2c1, and C2c3. An example of a type VI CRISPR/Cas endonuclease is C2c2. In some cases, a subject genome targeting composition includes a type V CRISPR/Cas endonuclease (e.g., Cpf1, C2c1, C2c3). In some cases, a Type V CRISPR/Cas endonuclease is a Cpf1 protein. In some cases, a subject genome targeting composition includes a type VI CRISPR/Cas endonuclease (e.g., C2c2)

Like type II CRISPR/Cas endonucleases, type V and VI CRISPR/Cas endonucleases form a complex with a corresponding guide RNA. The guide RNA provides target specificity to an endonuclease-guide RNA RNP complex by having a nucleotide sequence (a guide sequence) that is complementary to a sequence (the target site) of a target nucleic acid (as described elsewhere herein). The endonuclease of the complex provides the site-specific activity. In other words, the endonuclease is guided to a target site (e.g., stabilized at a target site) within a target nucleic acid sequence (e.g., a chromosomal sequence) by virtue of its association with the protein-binding segment of the guide RNA.

Examples and guidance related to type V and type VI CRISPR/Cas proteins (e.g., cpf1, C2c1, C2c2, and C2c3 guide RNAs) can be found in the art (see, e.g., Zetsche et al. (2015) *Cell*, 163(3):759-771; Makarova et al. (2015) *Nat. Rev. Microbiol.* 13(11): 722-736; Shmakov et al. (2015) *Mol. Cell,* 60(3):385-397; and the like).

In some cases, the Type V or type VI CRISPR/Cas endonuclease (e.g., Cpf1, C2c1, C2c2, C2c3) is enzymatically active, e.g., the Type V or type VI CRISPR/Cas protein, when bound to a guide RNA, and cleaves a target nucleic acid. In some cases, the Type V or type VI CRISPR/Cas endonuclease (e.g., Cpf1, C2c1, C2c2, C2c3) exhibits reduced enzymatic activity relative to a corresponding wild-type a Type V or type VI CRISPR/Cas endonuclease (e.g., Cpf1, C2c1, C2c2, C2c3), and retains DNA binding activity.

In some cases a type V CRISPR/Cas endonuclease is a Cpf1 protein or a functional portion thereof (see, e.g., UniProtKB-A0Q7Q2 (CPF1_FRATN)). Cpf1 protein is a member of the type V CRISPR system and is a polypeptide comprising about 1300 amino acids. Cpf1 contains a RuvC-like endonuclease domain. Unlike Cas9, Cpf1 cleaves target DNA in a staggered pattern using a single ribonuclease domain. The staggered DNA double-stranded break results in a 4 or 5-nt 5' overhang.

The CRISPR-Cpf1 system, identified in *Francisella* spp, is a class 2 CRISPR-Cas system that mediates robust DNA interference in human cells. Although functionally conserved, Cpf1 and Cas9 differ in many aspects including in their guide RNAs and substrate specificity (see, e.g., Fagerlund et al. (2015) *Genom. Bio.* 16: 251). A major difference between Cas9 and Cpf1 proteins is that Cpf1 does not utilize tracrRNA, and thus requires only a crRNA. The FnCpf1 crRNAs are 42-44 nucleotides long (19-nucleotide repeat and 23-25-nucleotide spacer) and contain a single stem-loop, which tolerates sequence changes that retain secondary structure. In addition, the Cpf1 crRNAs are significantly shorter than the ~100-nucleotide engineered sgRNAs required by Cas9, and the PAM requirements for FnCpf1 are 5'-TTN-3' and 5'-CTA-3' on the displaced strand. Although both Cas9 and Cpf1 make double strand breaks in the target DNA, Cas9 uses its RuvC- and HNH-like domains to make blunt-ended cuts within the seed sequence of the guide RNA, whereas Cpf1 uses a RuvC-like domain to produce staggered cuts outside of the seed. Because Cpf1 makes staggered cuts away from the critical seed region, NHEJ will not disrupt the target site, therefore ensuring that Cpf1 can continue to cut the same site until the desired HDR recombination event has taken place. Thus, in the methods and compositions described herein, it is understood that the term "Cas" includes both Cas9 and Cfp1 proteins. Accordingly, as used herein, a "CRISPR/Cas system" refers both CRISPR/Cas and/or CRISPR/Cfp1 systems, including both nuclease and/or transcription factor systems.

Accordingly, in certain embodiments the methods described herein the Cas protein is Cpf1 from any bacterial species or functional portion thereof. In some aspects Cpf1 is a *Francisella novicida* U112 protein or a functional portion thereof. In some aspects Cpf1 is a *Acidaminococcus* sp. BV3L6 protein or a functional portion thereof. In some aspects Cpf1 is a Lachnospiraceae bacterium ND2006 protein or a function portion thereof.

In certain embodiments, Cas protein may be a "functional portion" or "functional derivative" of a naturally occurring Cas protein, or of a modified Cas protein. A "functional derivative" of a native sequence polypeptide is a compound having a qualitative biological property in common with a native sequence polypeptide. "Functional derivatives" include, but are not limited to, fragments of a native sequence and derivatives of a native sequence polypeptide and its fragments, provided that they have a biological activity (e.g., endonuclease activity) in common with a corresponding native sequence polypeptide. As used herein, "functional portion" refers to a portion of a Cas protein that retains its ability to complex with at least one ribonucleic acid (e.g., guide RNA (gRNA)) and cleave a target polynucleotide sequence. In some embodiments, the functional portion comprises a combination of operably linked Cas9 protein functional domains selected from the group consisting of a DNA binding domain, at least one RNA binding domain, a helicase domain, and an endonuclease domain. In some embodiments, the functional portion comprises a combination of operably linked Cpf1 protein functional domains selected from the group consisting of a DNA binding domain, at least one RNA binding domain, a helicase domain, and an endonuclease domain. In some embodiments, the functional domains form a complex. In some embodiments, a functional portion of the Cas9 protein comprises a functional portion of a RuvC-like domain. In some embodiments, a functional portion of the Cas9 protein comprises a functional portion of the HNH nuclease domain. In some embodiments, a functional portion of the Cpf1 protein comprises a functional portion of a RuvC-like domain.

In certain embodiments a biological activity contemplated herein is the ability of the functional derivative to introduce a double strand break (DSB) at a desired target site in a genomic DNA. The term "derivative" encompasses both amino acid sequence variants of polypeptide, covalent modifications, and fusions thereof. In some aspects a functional derivative may comprise a single biological property of a naturally occurring Cas protein. In other aspects, a function derivative may comprise a subset of biological properties of a naturally occurring Cas protein.

In view of the foregoing, the term "Cas protein" as used herein encompasses a full-length Cas protein, an enzymatically active fragment of a Cas protein, and enzymatically active derivatives of a Cas protein or fragment thereof. Suitable derivatives of a Cas protein or a fragment thereof include but are not limited to, mutants, fusions, covalent modifications of Cas protein or a fragment thereof. Cas protein, which includes Cas protein or a fragment thereof, as well as derivatives of Cas protein or a fragment thereof, may be obtainable from a cell or synthesized chemically, recombinantly expressed, or by a combination of these procedures. The cell may be a cell that naturally produces Cas protein, or a cell that naturally produces Cas protein and is genetically engineered to produce the endogenous Cas protein at a higher expression level or to produce a Cas protein from an exogenously introduced nucleic acid, which nucleic acid encodes a Cas that is same or different from the endogenous Cas. In some case, the cell does not naturally produce Cas protein and is genetically engineered to produce a Cas protein.

In some embodiments, a Cas protein comprises one or more amino acid substitutions or modifications. In some embodiments, the one or more amino acid substitutions comprises a conservative amino acid substitution. In some instances, substitutions and/or modifications can prevent or reduce proteolytic degradation and/or extend the half-life of the polypeptide in a cell. In some embodiments, the Cas protein can comprise a peptide bond replacement (e.g., urea, thio urea, carbamate, sulfonyl urea, etc.). In some embodiments, the Cas protein can comprise a naturally occurring amino acid. In some embodiments, the Cas protein can comprise an alternative amino acid (e.g., D-amino acids, beta-amino acids, homocysteine, phosphoserine, etc.). In some embodiments, a Cas protein can comprise a modification to include a moiety (e.g., PEGylation, glycosylation, lipidation, acetylation, end-capping, etc.).

In certain embodiments the Cas protein used in the constructs described herein may be mutated to alter functionality. Illustrative selection methods, including phage display and two-hybrid systems, are disclosed in U.S. Pat.

Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in WO 02/077227.

In certain embodiments the Cas protein (e.g., Cas9 protein) comprise truncated Cas proteins. In one illustrative, but non-limiting, embodiment, the Cas9 comprises only the domain responsible for interaction with the crRNA or sgRNA and the target DNA.

In certain embodiments the Cas proteins comprising the constructs described herein comprise a Cas protein, or truncation thereof, fused to a different functional domain. In some aspects the functional domain is an activation or a repression domain. In other aspects, the functional domain is a nuclease domain. In some embodiments, the nuclease domain is a FokI endonuclease domain (see, e.g. Tsai (2014) Nat. Biotechnol. doi:10.1038/nbt.2908). In some embodiments, the FokI domain comprises mutations in the dimerization domain.

Guide RNA for Type II CRISPR/Cas Endonucleases (e.g., Cas9 gRNA)

A nucleic acid molecule that binds to a class 2 CRISPR/Cas endonuclease (e.g., a Cas9 protein, a type V or type VI CRISPR/Cas protein, a Cpf1 protein; etc.) and targets the complex to a specific location within a target nucleic acid is referred to herein as a "guide RNA" or "CRISPR/Cas guide nucleic acid" or "CRISPR/Cas guide RNA."

In various embodiments the guide RNA provides target specificity to the complex (the RNP complex) by including a targeting segment, which includes a guide sequence (also referred to herein as a targeting sequence), which typically comprise a nucleotide sequence that is complementary to a sequence of a target nucleic acid A guide RNA can be referred to by the protein to which it corresponds. For example, when the class 2 CRISPR/Cas endonuclease is a Cas9 protein, the corresponding guide RNA can be referred to as a "Cas9 guide RNA." Likewise, as another example, when the class 2 CRISPR/Cas endonuclease is a Cpf1 protein, the corresponding guide RNA can be referred to as a "Cpf1 guide RNA."

In some embodiments, a guide RNA includes two separate nucleic acid molecules (or two segments within a single molecule): an "activator" and a "targeter" and is referred to herein as a "dual guide RNA", a "double-molecule guide RNA", a "two-molecule guide RNA", or a "dgRNA." In some embodiments, the guide RNA is one molecule (e.g., for some class 2 CRISPR/Cas proteins, the corresponding guide RNA is a single molecule; and in some cases, an activator and targeter are covalently linked to one another, e.g., via intervening nucleotides and form different segments within a single RNA), and the guide RNA is referred to as a "single guide RNA", a "single-molecule guide RNA," a "one-molecule guide RNA", or simply "sgRNA." By "segment" it is meant a segment/section/region of a molecule, e.g., a contiguous stretch of nucleotides in a nucleic acid molecule. A segment can also mean a region/section of a complex such that a segment may comprise regions of more than one molecule.

In various embodiments the first segment (targeting segment) of a type II CRISPR/Cas endonuclease (e.g., a Cas9) guide RNA typically includes a nucleotide sequence (a guide sequence) that is complementary to (and therefore hybridizes with) a specific sequence (a target site) within a target nucleic acid (e.g., a target ssRNA, a target ssDNA, the complementary strand of a double stranded target DNA, etc.). The protein-binding segment (or "protein-binding sequence") interacts with (binds to) the endonuclease protein. The protein-binding segment of a subject Cas9 guide RNA typically includes two complementary stretches of nucleotides that hybridize to one another to form a double stranded RNA duplex (dsRNA duplex). Site-specific binding and/or cleavage of a target nucleic acid (e.g., genomic DNA) can occur at locations (e.g., target sequence of a target locus) determined by base-pairing complementarity between the Cas9 guide RNA (the guide sequence of the Cas9 guide RNA) and the target nucleic acid. I A Cas9 guide RNA and a Cas9 protein form a complex (e.g., bind via non-covalent interactions). The Cas9 guide RNA provides target specificity to the complex by including a targeting segment, which includes a guide sequence (a nucleotide sequence that is complementary to a sequence of a target nucleic acid). The Cas9 protein of the complex provides the site-specific activity (e.g., cleavage activity or an activity provided by the Cas9 protein when the Cas9 protein is a Cas9 fusion polypeptide, i.e., has a fusion partner). In other words, the Cas9 protein is guided to a target nucleic acid sequence (e.g., a target sequence in a chromosomal nucleic acid, e.g., a chromosome; a target sequence in an extrachromosomal nucleic acid, e.g., an episomal nucleic acid, a minicircle, an ssRNA, an ssDNA, etc.; a target sequence in a mitochondrial nucleic acid; a target sequence in a chloroplast nucleic acid; a target sequence in a plasmid; a target sequence in a viral nucleic acid; etc.) by virtue of its association with the Cas9 guide RNA.

The "guide sequence" also referred to as the "targeting sequence" of a type II CRISPR/Cas endonuclease guide RNA (e.g., Cas9 guide RNA) can be modified so that the guide RNA can target a CRISPR endonuclease protein to any desired sequence of any desired target nucleic acid, with the exception that the protospacer adjacent motif (PAM) sequence can be taken into account. Thus, for example, a Cas9 guide RNA can have a targeting segment with a sequence (a guide sequence) that has complementarity with (e.g., can hybridize to) a sequence in a nucleic acid in a eukaryotic cell, e.g., a viral nucleic acid, a eukaryotic nucleic acid (e.g., a eukaryotic chromosome, chromosomal sequence, a eukaryotic RNA, etc.), and the like.

In some embodiments, a Cas9 guide RNA includes two separate nucleic acid molecules: an "activator" and a "targeter" and is referred to herein as a "dual Cas9 guide RNA", a "double-molecule Cas9 guide RNA", or a "two-molecule Cas9 guide RNA" a "dual guide RNA", or a "dgRNA." In some embodiments, the activator and targeter are covalently linked to one another (e.g., via intervening nucleotides) and the guide RNA is referred to as a "single guide RNA", a "Cas9 single guide RNA", a "single-molecule Cas9 guide RNA," or a "one-molecule Cas9 guide RNA", or simply "sgRNA."

In various embodiments a Cas9 guide RNA comprises a crRNA-like ("CRISPR RNA"/"targeter"/"crRNA"/"crRNA repeat") molecule and a corresponding tracrRNA-like ("trans-acting CRISPR RNA"/"activator"/"tracrRNA") molecule. A crRNA-like molecule (targeter) typically comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator/tracrRNA) typically comprises a stretch of nucleotides (duplex-forming segment) that forms the other half of the dsRNA duplex of the protein-binding segment of the guide nucleic acid. In other words, a stretch of nucleotides of a crRNA-like molecule are complementary to and hybridize with a stretch of nucleotides of a tracrRNA-like molecule to form the dsRNA duplex of the protein-binding domain of the Cas9 guide RNA. As such, each targeter molecule can be said to have a corresponding activator molecule (which has a region that hybridizes with the targeter). In various embodiments the targeter molecule additionally provides the targeting segment. Thus, in various embodiments, a targeter and an activator molecule (as a corresponding pair) can hybridize to form a Cas9 guide RNA. The exact sequence of a given crRNA or tracrRNA molecule is characteristic of the species in which the RNA molecules are found. A subject dual Cas9 guide RNA can include any corresponding activator and targeter pair.

The term "activator" or "activator RNA" is used herein to mean a tracrRNA-like molecule (tracrRNA: "trans-acting CRISPR RNA") of a Cas9 dual guide RNA (and therefore of a Cas9 single guide RNA when the "activator" and the "targeter" are linked together by, e.g., intervening nucleotides). Thus, for example, a Cas9 guide RNA (dgRNA or sgRNA) typically comprises an activator sequence (e.g., a tracrRNA sequence). A tracr molecule (a tracrRNA) is a naturally existing molecule that hybridizes with a CRISPR RNA molecule (a crRNA) to form a Cas9 dual guide RNA. The term "activator" is used herein to encompass naturally existing tracrRNAs, but also to encompass tracrRNAs with modifications (e.g., truncations, sequence variations, base modifications, backbone modifications, linkage modifications, etc.) where the activator retains at least one function of a tracrRNA (e.g., contributes to the dsRNA duplex to which Cas9 protein binds). In some cases the activator provides one or more stem loops that can interact with Cas9 protein. An activator can be referred to as having a tracr sequence (tracrRNA sequence) and in some cases is a tracrRNA, but the term "activator" is not limited to naturally existing tracrRNAs.

The term "targeter" or "targeter RNA" is used herein to refer to a crRNA-like molecule (crRNA: "CRISPR RNA") of a Cas9 dual guide RNA (and therefore of a Cas9 single guide RNA when the "activator" and the "targeter" are linked together, e.g., by intervening nucleotides). Thus, for example, a Cas9 guide RNA (dgRNA or sgRNA) typically comprises a targeting segment (which includes nucleotides that hybridize with (are complementary to) a target nucleic acid, and a duplex-forming segment (e.g., a duplex forming segment of a crRNA, which can also be referred to as a crRNA repeat). Because the sequence of a targeting segment (the segment that hybridizes with a target sequence of a target nucleic acid) of a targeter is modified by a user to hybridize with a desired target nucleic acid, the sequence of a targeter will often be a non-naturally occurring sequence. However, in various embodiments, the duplex-forming segment of a targeter (described in more detail below), which hybridizes with the duplex-forming segment of an activator, can include a naturally existing sequence (e.g., can include the sequence of a duplex-forming segment of a naturally existing crRNA, which can also be referred to as a crRNA repeat). Thus, the term targeter is used herein to distinguish from naturally occurring crRNAs, despite the fact that part of a targeter (e.g., the duplex-forming segment) often includes a naturally occurring sequence from a crRNA. However, the term "targeter" encompasses naturally occurring crRNAs.

In various embodiments a Cas9 guide RNA can also be said to include 3 parts: (i) a targeting sequence (a nucleotide sequence that hybridizes with a sequence of the target nucleic acid); (ii) an activator sequence (as described above) (in some cases, referred to as a tracr sequence); and (iii) a sequence that hybridizes to at least a portion of the activator sequence to form a double stranded duplex. A targeter has (i) and (iii); while an activator has (ii).

A Cas9 guide RNA (e.g., a dual guide RNA or a single guide RNA) can be comprised of any corresponding activator and targeter pair. In some cases, the duplex forming segments can be swapped between the activator and the targeter. In other words, in some cases, the targeter includes a sequence of nucleotides from a duplex forming segment of a tracrRNA (which sequence would normally be part of an activator) while the activator includes a sequence of nucleotides from a duplex forming segment of a crRNA (which sequence would normally be part of a targeter).

As noted above, a targeter typically comprises both the targeting segment (single stranded) of the Cas9 guide RNA and a stretch ("duplex-forming segment") of nucleotides that forms one half of the dsRNA duplex of the protein-binding segment of the Cas9 guide RNA. A corresponding tracrRNA-like molecule (activator) typically comprises a stretch of nucleotides (a duplex-forming segment) that forms the other half of the dsRNA duplex of the protein-binding segment of the Cas9 guide RNA. In other words, a stretch of nucleotides of the targeter is complementary to and hybridizes with a stretch of nucleotides of the activator to form the dsRNA duplex of the protein-binding segment of a Cas9 guide RNA. As such, each targeter can be said to have a corresponding activator (which has a region that hybridizes with the targeter). The targeter molecule additionally provides the targeting segment. Thus, a targeter and an activator (as a corresponding pair) hybridize to form a Cas9 guide RNA. The particular sequence of a given naturally existing crRNA or tracrRNA molecule is characteristic of the species in which the RNA molecules are found. Examples of suitable activator and targeter are well known in the art.

In various embodiments a Cas9 guide RNA (e.g., a dual guide RNA or a single guide RNA) can be comprised of any corresponding activator and targeter pair.

Targeting Segment of a Type II CRISPR Endonuclease (e.g, Cas9) Guide RNA

The first segment of a subject guide nucleic acid typically includes a guide sequence (e.g., a targeting sequence) a nucleotide sequence that is complementary to a sequence (a target site) in a target nucleic acid). In other words, the targeting segment of a subject guide nucleic acid can interact with a target nucleic acid (e.g., double stranded DNA (dsDNA)) in a sequence-specific manner via hybridization (i.e., base pairing). As such, the nucleotide sequence of the targeting segment may vary (depending on the target) and can determine the location within the target nucleic acid that the Cas9 guide RNA and the target nucleic acid will interact. The targeting segment of a Cas9 guide RNA can be modified (e.g., by genetic engineering)/designed to hybridize to any desired sequence (target site) within a target nucleic acid (e.g., a eukaryotic target nucleic acid such as genomic DNA).

In certain embodiments the targeting segment can have a length of 7 or more nucleotides (nt) (e.g., 8 or more, 9 or more, 10 or more, 12 or more, 15 or more, 20 or more, 25 or more, 30 or more, or 40 or more nucleotides). In some cases, the targeting segment can have a length of from 7 to 100 nucleotides (nt) (e.g., from 7 to 80 nt, from 7 to 60 nt, from 7 to 40 nt, from 7 to 30 nt, from 7 to 25 nt, from 7 to 22 nt, from 7 to 20 nt, from 7 to 18 nt, from 8 to 80 nt, from 8 to 60 nt, from 8 to 40 nt, from 8 to 30 nt, from 8 to 25 nt, from 8 to 22 nt, from 8 to 20 nt, from 8 to 18 nt, from 10 to 100 nt, from 10 to 80 nt, from 10 to 60 nt, from 10 to 40 nt, from 10 to 30 nt, from 10 to 25 nt, from 10 to 22 nt, from 10 to 20 nt, from 10 to 18 nt, from 12 to 100 nt, from 12 to 80 nt, from 12 to 60 nt, from 12 to 40 nt, from 12 to 30 nt, from 12 to 25 nt, from 12 to 22 nt, from 12 to 20 nt, from 12 to 18 nt, from 14 to 100 nt, from 14 to 80 nt, from 14 to 60 nt, from 14 to 40 nt, from 14 to 30 nt, from 14 to 25 nt, from 14 to 22 nt, from 14 to 20 nt, from 14 to 18 nt, from 16 to 100 nt, from 16 to 80 nt, from 16 to 60 nt, from 16 to 40 nt, from 16 to 30 nt, from 16 to 25 nt, from 16 to 22 nt, from 16 to 20 nt, from 16 to 18 nt, from 18 to 100 nt, from 18 to 80 nt, from 18 to 60 nt, from 18 to 40 nt, from 18 to 30 nt, from 18 to 25 nt, from 18 to 22 nt, or from 18 to 20 nt).

The nucleotide sequence (the targeting sequence) of the targeting segment that is complementary to a nucleotide sequence (target site) of the target nucleic acid can have a length of 10 nt or more. For example, the targeting sequence of the targeting segment that is complementary to a target site of the target nucleic acid can have a length of 12 nt or more, 15 nt or more, 18 nt or more, 19 nt or more, or 20 nt or more. In some cases, the nucleotide sequence (the targeting sequence) of the targeting segment that is complementary to a nucleotide sequence (target site) of the target nucleic acid has a length of 12 nt or more. In some cases, the nucleotide sequence (the targeting sequence) of the targeting segment that is complementary to a nucleotide sequence (target site) of the target nucleic acid has a length of 18 nt or more.

For example, in certain embodiments, the targeting sequence of the targeting segment that is complementary to a target sequence of the target nucleic acid can have a length of from 10 to 100 nucleotides (nt) (e.g., from 10 to 90 nt, from 10 to 75 nt, from 10 to 60 nt, from 10 to 50 nt, from 10 to 35 nt, from 10 to 30 nt, from 10 to 25 nt, from 10 to 22 nt, from 10 to 20 nt, from 12 to 100 nt, from 12 to 90 nt, from 12 to 75 nt, from 12 to 60 nt, from 12 to 50 nt, from 12 to 35 nt, from 12 to 30 nt, from 12 to 25 nt, from 12 to 22 nt, from 12 to 20 nt, from 15 to 100 nt, from 15 to 90 nt, from 15 to 75 nt, from 15 to 60 nt, from 15 to 50 nt, from 15 to 35 nt, from 15 to 30 nt, from 15 to 25 nt, from 15 to 22 nt, from 15 to 20 nt, from 17 to 100 nt, from 17 to 90 nt, from 17 to 75 nt, from 17 to 60 nt, from 17 to 50 nt, from 17 to 35 nt, from 17 to 30 nt, from 17 to 25 nt, from 17 to 22 nt, from 17 to 20 nt, from 18 to 100 nt, from 18 to 90 nt, from 18 to 75 nt, from 18 to 60 nt, from 18 to 50 nt, from 18 to 35 nt, from 18 to 30 nt, from 18 to 25 nt, from 18 to 22 nt, or from 18 to 20 nt). In some cases, the targeting sequence of the targeting segment that is complementary to a target sequence of the target nucleic acid has a length of from 15 nt to 30 nt. In some cases, the targeting sequence of the targeting segment that is complementary to a target sequence of the target nucleic acid has a length of from 15 nt to 25 nt. In some cases, the targeting sequence of the targeting segment that is complementary to a target sequence of the target nucleic acid has a length of from 18 nt to 30 nt. In some cases, the targeting sequence of the targeting segment that is complementary to a target sequence of the target nucleic acid has a length of from 18 nt to 25 nt. In some cases, the targeting sequence of the targeting segment that is complementary to a target sequence of the target nucleic acid has a length of from 18 nt to 22 nt. In some cases, the targeting sequence of the targeting segment that is complementary to a target site of the target nucleic acid is 20 nucleotides in length. In some cases, the targeting sequence of the targeting segment that is complementary to a target site of the target nucleic acid is 19 nucleotides in length.

In certain embodiments the percent complementarity between the targeting sequence (guide sequence) of the targeting segment and the target site of the target nucleic acid can be 60% or more (e.g., 65% or more, 70% or more, 75% or more, 80% or more, 85% or more, 90% or more, 95% or more, 97% or more, 98% or more, 99% or more, or 100%). In some cases, the percent complementarity between the targeting sequence of the targeting segment and the target site of the target nucleic acid is 100% over the seven contiguous 5'-most nucleotides of the target site of the target nucleic acid. In some cases, the percent complementarity between the targeting sequence of the targeting segment and the target site of the target nucleic acid is 60% or more over about 20 contiguous nucleotides. In some cases, the percent complementarity between the targeting sequence of the targeting segment and the target site of the target nucleic acid is 100% over the fourteen contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the seven contiguous 5'-most nucleotides of the target site of the target nucleic acid and as low as 0% or more over the remainder. In such a case, the targeting sequence can be considered to be 20 nucleotides in length.

In some cases, the percent complementarity between the targeting sequence of the targeting segment and the target site of the target nucleic acid is 100% over the 7 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 8 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 9 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 10 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 17 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 100% over the 18 contiguous 5'-most nucleotides of the target site of the target nucleic acid (which can be complementary to the 3'-most nucleotides of the targeting sequence of the Cas9 guide RNA). In some cases, the percent complementarity between the targeting sequence of the targeting segment and the target site of the target nucleic acid is 60% or more (e.g., e.g., 65% or more, 70% or more, 75% or more, 80% or more, 85% or more, 90% or more, 95% or more, 97% or more, 98% or more, 99% or more, or 100%) over about 20 contiguous nucleotides.

In some cases, the percent complementarity between the targeting sequence of the targeting segment and the target site of the target nucleic acid is 100% over the 7 contiguous 5'-most nucleotides of the target site of the target nucleic acid and as low as 0% or more over the remainder. In such a case, the targeting sequence can be considered to be 7 nucleotides in length. In some cases, the percent complementarity between the targeting sequence of the targeting segment and the target site of the target nucleic acid is 100% over the 8 contiguous 5'-most nucleotides of the target site of the target nucleic acid and as low as 0% or more over the remainder. In such a case, the targeting sequence can be considered to be 8 nucleotides in length. In some cases, the percent complementarity between the targeting sequence of the targeting segment and the target site of the target nucleic acid is 100% over the 9 contiguous 5'-most nucleotides of the target site of the target nucleic acid and as low as 0% or more over the remainder. In such a case, the targeting sequence can be considered to be 9 nucleotides in length. In some cases, the percent complementarity between the targeting sequence of the targeting segment and the target site of the target nucleic acid is 100% over the 10 contiguous 5'-most nucleotides of the target site of the target nucleic acid and as low as 0% or more over the remainder. In such a case, the targeting sequence can be considered to be 10 nucleotides in length. In some cases, the percent complementarity between the targeting sequence of the targeting segment and the target site of the target nucleic acid is 100% over the 11 contiguous 5'-most nucleotides of the target site of the target nucleic acid and as low as 0% or more over the remainder. In such a case, the targeting sequence can be considered to be 11 nucleotides in length. In some cases, the percent complementarity between the targeting sequence of the targeting segment and the target site of the target nucleic acid is 100% over the 12 contiguous 5'-most nucleotides of the target site of the target nucleic acid and as low as 0% or more over the remainder. In such a case, the targeting sequence can be considered to be 12 nucleotides in length. In some cases, the percent complementarity between the targeting sequence of the targeting segment and the target site of the target nucleic acid is 100% over the 13 contiguous 5'-most nucleotides of the target site of the target nucleic acid and as low as 0% or more over the remainder. In such a case, the targeting sequence can be considered to be 13 nucleotides in length. In some cases, the percent complementarity between the targeting sequence of the targeting segment and the target site of the target nucleic acid is 100% over the 14 contiguous 5'-most nucleotides of the target site of the target nucleic acid and as low as 0% or more over the remainder. In such a case, the targeting sequence can be considered to be 14 nucleotides in length. In some cases, the percent complementarity between the targeting sequence of the targeting segment and the target site of the target nucleic acid is 100% over the 17 contiguous 5'-most nucleotides of the target site of the target nucleic acid and as low as 0% or more over the remainder. In such a case, the targeting sequence can be considered to be 17 nucleotides in length. In some cases, the percent complementarity between the targeting sequence of the targeting segment and the target site of the target nucleic acid is 100% over the 18 contiguous 5'-most nucleotides of the target site of the target nucleic acid and as low as 0% or more over the remainder. In such a case, the targeting sequence can be considered to be 18 nucleotides in length.

Protein-Binding Segment of a Type II CRISPR Endonuclease (e.g., Cas9) Guide RNA

The protein-binding segment of a Cas9 guide RNA typically interacts with a Cas9 protein. The Cas9 guide RNA guides the bound Cas9 protein to a specific nucleotide sequence within target nucleic acid via the above mentioned targeting segment. The protein-binding segment of a Cas9 guide RNA typically comprises two stretches of nucleotides that are complementary to one another and hybridize to form a double stranded RNA duplex (dsRNA duplex). Thus, the protein-binding segment can include a dsRNA duplex. In some cases, the protein-binding segment also includes stem loop 1 (the "nexus") of a Cas9 guide RNA. For example, in some cases, the activator of a Cas9 guide RNA (dgRNA or sgRNA) includes (i) a duplex forming segment that contributes to the dsRNA duplex of the protein-binding segment; and (ii) nucleotides 3' of the duplex forming segment, e.g., that form stem loop 1 (the "nexus"). For example, in some cases, the protein-binding segment includes stem loop 1 (the "nexus") of a Cas9 guide RNA. In some cases, the protein-binding segment includes 5 or more nucleotides (nt) (e.g., 6 or more, 7 or more, 8 or more, 9 or more, 10 or more, 11 or more, 12 or more, 15 or more, 20 or more, 30 or more, 40 or more, 50 or more, 60 or more, 70 or more, 75 or more, or 80 or more nt) 3' of the dsRNA duplex (where 3' is relative to the duplex-forming segment of the activator sequence).

The dsRNA duplex of the guide RNA (sgRNA or dgRNA) that forms between the activator and targeter is sometimes referred to herein as the "stem loop". In addition, the activator (activator RNA, tracrRNA) of many naturally existing Cas9 guide RNAs (e.g., S. pygogenes guide RNAs) has 3 stem loops (3 hairpins) that are 3' of the duplex-forming segment of the activator. The closest stem loop to the duplex-forming segment of the activator (3' of the duplex forming segment) is called "stem loop 1" (and is also referred to herein as the "nexus"); the next stem loop is called "stem loop 2" (and is also referred to herein as the "hairpin 1"); and the next stem loop is called "stem loop 3" (and is also referred to herein as the "hairpin 2").

In some cases, a Cas9 guide RNA (sgRNA or dgRNA) (e.g., a full length Cas9 guide RNA) has stem loops 1, 2, and 3. In some cases, an activator (of a Cas9 guide RNA) has stem loop 1, but does not have stem loop 2 and does not have stem loop 3. In some cases, an activator (of a Cas9 guide RNA) has stem loop 1 and stem loop 2, but does not have stem loop 3. In some cases, an activator (of a Cas9 guide RNA) has stem loops 1, 2, and 3.

In some cases, the activator (e.g., tracr sequence) of a Cas9 guide RNA (dgRNA or sgRNA) includes (i) a duplex forming segment that contributes to the dsRNA duplex of the protein-binding segment; and (ii) a stretch of nucleotides (e.g., referred to herein as a 3' tail) 3' of the duplex forming segment. In some cases, the additional nucleotides 3' of the duplex forming segment form stem loop 1. In some cases, the activator (e.g., tracr sequence) of a Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) 3' of the duplex forming segment. In some cases, the activator (activator RNA) of a Cas9 guide RNA (dgRNA or sgRNA) includes (i) a duplex forming segment that contributes to the dsRNA duplex of the protein-binding segment; and (ii) 5 or more nucleotides (e.g., 6 or more, 7 or more, 8 or more, 9 or more, 10 or more, 11 or more, 12 or more, 13 or more, 14 or more, 15 or more, 20 or more, 25 or more, 30 or more, 35 or more, 40 or more, 45 or more, 50 or more, 60 or more, 70 or more, or 75 or more nucleotides) 3' of the duplex forming segment.

In some cases, the activator (e.g., tracr sequence) of a Cas9 guide RNA (dgRNA or sgRNA) includes (i) a duplex forming segment that contributes to the dsRNA duplex of the protein-binding segment; and (ii) a stretch of nucleotides (e.g., referred to herein as a 3' tail) 3' of the duplex forming segment. In some cases, the stretch of nucleotides 3' of the duplex forming segment has a length in a range of from 5 to 200 nucleotides (nt) (e.g., from 5 to 150 nt, from 5 to 130 nt, from 5 to 120 nt, from 5 to 100 nt, from 5 to 80 nt, from 10 to 200 nt, from 10 to 150 nt, from 10 to 130 nt, from 10 to 120 nt, from 10 to 100 nt, from 10 to 80 nt, from 12 to 200 nt, from 12 to 150 nt, from 12 to 130 nt, from 12 to 120 nt, from 12 to 100 nt, from 12 to 80 nt, from 15 to 200 nt, from 15 to 150 nt, from 15 to 130 nt, from 15 to 120 nt, from 15 to 100 nt, from 15 to 80 nt, from 20 to 200 nt, from 20 to 150 nt, from 20 to 130 nt, from 20 to 120 nt, from 20 to 100 nt, from 20 to 80 nt, from 30 to 200 nt, from 30 to 150 nt, from 30 to 130 nt, from 30 to 120 nt, from 30 to 100 nt, or from 30 to 80 nt). In some cases, the nucleotides of the 3' tail of an activator RNA are wild type sequences. It will be recognized that a number of different alternative sequences can be used.

Examples of various Cas9 proteins and Cas9 guide RNAs (as well as information regarding requirements related to protospacer adjacent motif (PAM) sequences present in targeted nucleic acids) can be found in the art (see, e.g., Jinek et al. (2012) Science, 337(6096): 816-821; Chylinski et al. (2013) RNA Biol. 10(5):726-737; Ma et al., (2013) Biomed. Res. Int. 2013: 270805; Hou et al. (2013) Proc. Natl. Acad. Sci. USA, 110(39): 15644-15649; Pattanayak et al. (2013) Nat. Biotechnol. 31(9): 839-843; Qi et al. (2013) Cell, 152(5): 1173-1183; Wang et al. (2013) Cell, 153(4): 910-918; Chen et. al. (2013) Nucl. Acids Res. 41(20): e19; Cheng et. al. (2012) Cell Res. 23(10): 1163-1171; Cho et. al. (2013) Genetics, 195(3): 1177-1180; DiCarlo et al. (2013) Nucl. Acids Res. 41(7): 4336-4343; Dickinson et. al. (2013) Nat. Meth. 10(10): 1028-1034; Ebina et. al. (2013) Sci. Rep. 3: 2510; Fujii et. al. (2013) Nucl. Acids Res. 41(20): e187; Hu et. al. (2013) Cell Res. 23(11): 1322-1325; Jiang et. al. (2013) Nucl. Acids Res. 41(20): e188; Larson et. al. (2013) Nat. Protoc. 8(11): 2180-2196; Mali et. at. (2013) Nat. Meth. 10(10): 957-963; Nakayama et. al. (2013) Genesis, 51(12): 835-843; Ran et. al. (2013) Nat. Protoc. 8(11): 2281-2308; Ran et. al. (2013) Cell 154(6): 1380-1389; Walsh et. al. (2013) Proc. Natl. Acad. Sci. USA, 110(39): 15514-15515; Yang et. al. (2013) Cell, 154(6): 1370-1379; Briner et al. (2014)Mol. Cell, 56(2): 333-339; and U.S. Pat. Nos. 8,906,616; 8,895,308; 8,889,418; 8,889,356; 8,871,445; 8,865,406; 8,795,965; 8,771,945; 8,697,359; 2014/0068797; 2014/0170753; 2014/0179006; 2014/0179770; 2014/0186843; 2014/0186919; 2014/0186958; 2014/0189896; 2014/0227787; 2014/0234972; 2014/0242664; 2014/0242699; 2014/0242700; 2014/0242702; 2014/0248702; 2014/0256046; 2014/0273037; 2014/0273226; 2014/0273230; 2014/0273231; 2014/0273232; 2014/0273233; 2014/0273234; 2014/0273235; 2014/0287938; 2014/0295556; 2014/0295557; 2014/0298547; 2014/0304853; 2014/0309487; 2014/0310828; 2014/0310830; 2014/0315985; 2014/0335063; 2014/0335620; 2014/0342456; 2014/0342457; 2014/0342458; 2014/0349400; 2014/0349405; 2014/0356867; 2014/0356956; 2014/0356958; 2014/0356959; 2014/0357523; 2014/0357530; 2014/0364333; and 2014/0377868; all of which are incorporated herein by reference in their entirety.

In certain embodiments alternative PAM sequences may also be utilized, where a PAM sequence can be NAG as an alternative to NGG (Hsu (2014) supra.) using an S. pyogenes Cas9. Additional PAM sequences may also include those lacking the initial G (see, e.g., Sander & Joung (2014) Nature Biotech 32(4):347). In addition to the S. pyogenes encoded Cas9 PAM sequences, other PAM sequences can be used that are specific for Cas9 proteins from other bacterial sources. For example, the PAM sequences shown below in Table 5 (adapted from Sander and Joung, supra., and Esvelt et al. (2013) Nat. Meth. 10(11): 1116) are specific for these Cas9 proteins:

TABLE 5

Illustrative PAM sequences from various species.

| Species | PAM | SEQ ID NO |
|---|---|---|
| S. pyogenes | NGG | |
| S. pyogenes | NAG | |
| S. mutans | NGG | |
| S. thermophilus | NGGNG | 19 |
| S. thermophilus | NNAAAW | 20 |
| S. thermophilus | NNAGAA | 21 |
| S. thermophilus | NNNGATT | 22 |
| C. jejuni | NNNNACA | 23 |
| N. meningitides | NNNNGATT | 24 |
| P. multocida | GNNNCNNA | 25 |
| F. novicida | NG | |

Thus, in certain embodiments, a suitable target sequence for use with a S. pyogenes CRISPR/Cas system can be chosen according to the following guideline: [n17, n18, n19, or n20](G/A)G (SEQ ID NO:26). Alternatively, in certain embodiments, the PAM sequence can follow the guideline G[n17, n18, n19, n20](G/A)G (SEQ ID NO:27). For Cas9 proteins derived from non-S. pyogenes bacteria, the same guidelines may be used where the alternate PAMs are substituted in for the S. pyogenes PAM sequences.

Guide RNAs for Type V and Type VI CRISPR/Cas Endonucleases (e.g., Cpf1 Guide RNA)

A guide RNA that binds to a type V or type VI CRISPR/Cas protein (e.g., Cpf1, C2c1, C2c2, C2c3), and targets the complex to a specific location within a target nucleic acid is referred to herein generally as a "type V or type VI CRISPR/Cas guide RNA". An example of a more specific term is a "Cpf1 guide RNA."

In various embodiments a type V or type VI CRISPR/Cas guide RNA (e.g., cpf1 guide RNA) can have a total length of from 30 nucleotides (nt) to 200 nt, e.g., from 30 nt to 180 nt, from 30 nt to 160 nt, from 30 nt to 150 nt, from 30 nt to 125 nt, from 30 nt to 100 nt, from 30 nt to 90 nt, from 30 nt to 80 nt, from 30 nt to 70 nt, from 30 nt to 60 nt, from 30 nt to 50 nt, from 50 nt to 200 nt, from 50 nt to 180 nt, from 50 nt to 160 nt, from 50 nt to 150 nt, from 50 nt to 125 nt, from 50 nt to 100 nt, from 50 nt to 90 nt, from 50 nt to 80 nt, from 50 nt to 70 nt, from 50 nt to 60 nt, from 70 nt to 200 nt, from 70 nt to 180 nt, from 70 nt to 160 nt, from 70 nt to 150 nt, from 70 nt to 125 nt, from 70 nt to 100 nt, from 70 nt to 90 nt, or from 70 nt to 80 nt). In some cases, a type V or type VI CRISPR/Cas guide RNA (e.g., cpf1 guide RNA) has a total length of at least 30 nt (e.g., at least 40 nt, at least 50 nt, at least 60 nt, at least 70 nt, at least 80 nt, at least 90 nt, at least 100 nt, or at least 120 nt).

In some cases, a Cpf1 guide RNA has a total length of 35 nt, 36 nt, 37 nt, 38 nt, 39 nt, 40 nt, 41 nt, 42 nt, 43 nt, 44 nt, 45 nt, 46 nt, 47 nt, 48 nt, 49 nt, or 50 nt.

Like a Cas9 guide RNA, a type V or type VI CRISPR/Cas guide RNA (e.g., cpf1 guide RNA) can include a target nucleic acid-binding segment and a duplex-forming region (e.g., in some cases formed from two duplex-forming segments, i.e., two stretches of nucleotides that hybridize to one another to form a duplex)

In various embodiments the target nucleic acid-binding segment of a type V or type VI CRISPR/Cas guide RNA (e.g., cpf1 guide RNA) can have a length of from 15 nt to 30 nt, e.g., 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt. In some cases, the target nucleic acid-binding segment has a length of 23 nt. In some cases, the target nucleic acid-binding segment has a length of 24 nt. In some cases, the target nucleic acid-binding segment has a length of 25 nt.

In certain embodiments the guide sequence of a type V or type VI CRISPR/Cas guide RNA (e.g., cpf1 guide RNA) can have a length of from 15 nt to 30 nt (e.g., 15 to 25 nt, 15 to 24 nt, 15 to 23 nt, 15 to 22 nt, 15 to 21 nt, 15 to 20 nt, 15 to 19 nt, 15 to 18 nt, 17 to 30 nt, 17 to 25 nt, 17 to 24 nt, 17 to 23 nt, 17 to 22 nt, 17 to 21 nt, 17 to 20 nt, 17 to 19 nt, 17 to 18 nt, 18 to 30 nt, 18 to 25 nt, 18 to 24 nt, 18 to 23 nt, 18 to 22 nt, 18 to 21 nt, 18 to 20 nt, 18 to 19 nt, 19 to 30 nt, 19 to 25 nt, 19 to 24 nt, 19 to 23 nt, 19 to 22 nt, 19 to 21 nt, 19 to 20 nt, 20 to 30 nt, 20 to 25 nt, 20 to 24 nt, 20 to 23 nt, 20 to 22 nt, 20 to 21 nt, 15 nt, 16 nt, 17 nt, 18 nt, 19 nt, 20 nt, 21 nt, 22 nt, 23 nt, 24 nt, 25 nt, 26 nt, 27 nt, 28 nt, 29 nt, or 30 nt). In some cases, the guide sequence has a length of 17 nt. In some cases, the guide sequence has a length of 18 nt. In some cases, the guide sequence has a length of 19 nt. In some cases, the guide sequence has a length of 20 nt. In some cases, the guide sequence has a length of 21 nt. In some cases, the guide sequence has a length of 22 nt. In some cases, the guide sequence has a length of 23 nt. In some cases, the guide sequence has a length of 24 nt.

In certain embodiments the guide sequence of a type V or type VI CRISPR/Cas guide RNA (e.g., cpf1 guide RNA) can have 100% complementarity with a corresponding length of target nucleic acid sequence. The guide sequence can have less than 100% complementarity with a corresponding length of target nucleic acid sequence. For example, the guide sequence of a type V or type VI CRISPR/Cas guide RNA (e.g., cpf1 guide RNA) can have 1, 2, 3, 4, or 5 nucleotides that are not complementary to the target nucleic acid sequence. For example, in some cases, where a guide sequence has a length of 25 nucleotides, and the target nucleic acid sequence has a length of 25 nucleotides, in some cases, the target nucleic acid-binding segment has 100% complementarity to the target nucleic acid sequence. As another example, in some cases, where a guide sequence has a length of 25 nucleotides, and the target nucleic acid sequence has a length of 25 nucleotides, in some cases, the target nucleic acid-binding segment has 1 non-complementary nucleotide and 24 complementary nucleotides with the target nucleic acid sequence. As another example, in some cases, where a guide sequence has a length of 25 nucleotides, and the target nucleic acid sequence has a length of 25 nucleotides, in some cases, the target nucleic acid-binding segment has 2 non-complementary nucleotides and 23 complementary nucleotides with the target nucleic acid sequence.

In certain embodiments the duplex-forming segment of a type V or type VI CRISPR/Cas guide RNA (e.g., cpf1 guide RNA) (e.g., of a targeter RNA or an activator RNA) can have a length of from 15 nt to 25 nt (e.g., 15 nt, 16 nt, 17 nt, 18 nt, 19 nt, 20 nt, 21 nt, 22 nt, 23 nt, 24 nt, or 25 nt).

The RNA duplex of a type V or type VI CRISPR/Cas guide RNA (e.g., cpf1 guide RNA) can have a length of from 5 base pairs (bp) to 40 bp (e.g., from 5 to 35 bp, 5 to 30 bp, 5 to 25 bp, 5 to 20 bp, 5 to 15 bp, 5-12 bp, 5-10 bp, 5-8 bp, 6 to 40 bp, 6 to 35 bp, 6 to 30 bp, 6 to 25 bp, 6 to 20 bp, 6 to 15 bp, 6 to 12 bp, 6 to 10 bp, 6 to 8 bp, 7 to 40 bp, 7 to 35 bp, 7 to 30 bp, 7 to 25 bp, 7 to 20 bp, 7 to 15 bp, 7 to 12 bp, 7 to 10 bp, 8 to 40 bp, 8 to 35 bp, 8 to 30 bp, 8 to 25 bp, 8 to 20 bp, 8 to 15 bp, 8 to 12 bp, 8 to 10 bp, 9 to 40 bp, 9 to 35 bp, 9 to 30 bp, 9 to 25 bp, 9 to 20 bp, 9 to 15 bp, 9 to 12 bp, 9 to 10 bp, 10 to 40 bp, 10 to 35 bp, 10 to 30 bp, 10 to 25 bp, 10 to 20 bp, 10 to 15 bp, or 10 to 12 bp).

As an illustrative, but non-limiting example, a duplex-forming segment of a Cpf1 guide RNA can comprise a nucleotide sequence selected from (5' to 3'):

```
                                        (SEQ ID NO: 28)
            AAUUUCUACUGUUGUAGAU, (SEQ ID NO: 29)
            AAUUUCUGCUGUUGCAGAU, (SEQ ID NO: 30)
            AAUUUCCACUGUUGUGGAU, (SEQ ID NO: 31)
            AAUUCCUACUGUUGUAGGU, (SEQ ID NO: 32)
            AAUUUCUACUAUUGUAGAU, (SEQ ID NO: 33)
            AAUUUCUACUGCUGUAGAU, (SEQ ID NO: 34)
            AAUUUCUACUUUGUAGAU, (SEQ ID NO: 35)
            AAUUUCUACUUGUAGAU,
``` and the like. The guide sequence can then follow (5' to 3') the duplex forming segment.

Examples and guidance related to type V or type VI CRISPR/Cas endonucleases and guide RNAs (as well as information regarding requirements related to protospacer adjacent motif (PAM) sequences present in targeted nucleic acids) can be found in the art (see, e.g., Zetsche et al. (2015) *Cell*, 163(3): 759-771; Makarova et al. (2015) *Nat. Rev. Microbiol.* 13(11): 722-736; Shmakov et al. (2015)*Mol. Cell*, 60(3): 385-397; and the like).

Zinc Finger Endonucleases.

In certain embodiments the targeted endonuclease comprises a zinc finger nuclease (ZFN). Typically, a zinc finger nuclease comprises a DNA binding domain (e.g., zinc finger) and a cleavage domain (e.g., nuclease), both of which are described below.

Zinc Finger Binding Domain.

Zinc finger binding domains may be engineered to recognize and bind to any nucleic acid sequence of choice (see, e.g., Beerli et al. (2002) *Nat. Biotechnol.* 20: 135-141; Pabo et al. (2001) *Ann. Rev. Biochem.* 70: 313-340; Isalan et al. (2001) *Nat. Biotechnol.* 19: 656-660; Segal et al. (2001)

*Curr. Opin. Biotechnol.* 12: 632-637; Choo et al. (2000) *Curr. Opin. Struct. Biol.* 10: 411-416; Zhang et al. (2000) *J. Biol. Chem.* 275(43): 33850-33860; Doyon et al. (2008) *Nat. Biotechnol.* 26: 702-708; and Santiago et al. (2008) *Proc. Natl. Acad. Sci. USA*, 105: 5809-5814). An engineered zinc finger binding domain can have a novel binding specificity compared to a naturally-occurring zinc finger protein. Engineering methods include, but are not limited to, rational design and various types of selection. Rational design includes, for example, using databases comprising doublet, triplet, and/or quadruplet nucleotide sequences and individual zinc finger amino acid sequences, in which each doublet, triplet or quadruplet nucleotide sequence is associated with one or more amino acid sequences of zinc fingers which bind the particular triplet or quadruplet sequence (see, e.g., U.S. Pat. Nos. 6,453,242 and 6,534,261, and the like). As an example, the algorithm described in U.S. Pat. No. 6,453,242 may be used to design a zinc finger binding domain to target a preselected sequence. Alternative methods, such as rational design using a nondegenerate recognition code table can also be used to design a zinc finger binding domain to target a specific sequence (see, e.g., Sera et al. (2002) *Biochemistry* 41: 7074-7081; and the like). Publicly available web-based tools for identifying target sites in DNA sequences and designing zinc finger binding domains are found, inter alia, at www.zincfingertools.org and zifit.partners.org/ZiFiT/(see also Mandell et al. (2006) *Nucl. Acids Res.* 34: W516-W523; Sander et al. (2007) *Nucl. Acids Res.* 35: W599-W605; and the like).

A zinc finger binding domain may be designed to recognize and bind a DNA sequence ranging from about 3 nucleotides to about 21 nucleotides in length, for example, from about 9 to about 18 nucleotides in length. Each zinc finger recognition region (i.e., zinc finger) typically recognizes and binds three nucleotides. In certain embodiments, the zinc finger binding domains of suitable targeted zinc finger nucleases comprise at least three zinc finger recognition regions (i.e., zinc fingers). The zinc finger binding domain, however, may comprise four, or five, or six, or more zinc finger recognition regions. A zinc finger binding domain may be designed to bind to any suitable target DNA sequence (see, e.g., U.S. Pat. Nos. 6,607,882; 6,534,261, 6,453,242, and the like.

Illustrative methods of selecting a zinc finger recognition region include, but are not limited to phage display and two-hybrid systems, and are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237y. In addition, enhancement of binding specificity for zinc finger binding domains has been described, for example, in WO 02/077227.

Zinc finger binding domains and methods for design and construction of fusion proteins (and polynucleotides encoding same) are known to those of skill in the art and are described in detail in U.S. Patent Application Publication Nos. 2005/0064474 and 2006/0188987. Zinc finger recognition regions and/or multi-fingered zinc finger proteins may be linked together using suitable linker sequences, including for example, linkers of five or more amino acids in length (see, e.g., U.S. Pat. Nos. 6,479,626; 6,903,185; and 7,153, 949) for non-limiting examples of linker sequences of six or more amino acids in length.

Cleavage Domain.

A zinc finger nuclease also typically includes a cleavage domain. The cleavage domain portion of the zinc finger nuclease may be obtained from any endonuclease or exonuclease. Non-limiting examples of endonucleases from which a cleavage domain may be derived include, but are not limited to, restriction endonucleases and homing endonucleases (see, e.g., New England Biolabs catalog (www.neb.com); Belfort et al. (1997) *Nucleic Acids Res.* 25:3379-3388; and the like). Additional enzymes that cleave DNA are known (e.g., S1 Nuclease; mung bean nuclease; pancreatic DNase I; micrococcal nuclease; yeast HO endonuclease). In certain embodiments one or more of these enzymes (or functional fragments thereof) may be used as a source of cleavage domains.

In certain embodiments, a cleavage domain also may be derived from an enzyme or portion thereof, as described above, that requires dimerization for cleavage activity. Two zinc finger nucleases may be required for cleavage, as each nuclease comprises a monomer of the active enzyme dimer. Alternatively, a single zinc finger nuclease can comprise both monomers to create an active enzyme dimer. As used herein, an "active enzyme dimer" is an enzyme dimer capable of cleaving a nucleic acid molecule. The two cleavage monomers may be derived from the same endonuclease (or functional fragments thereof), or each monomer may be derived from a different endonuclease (or functional fragments thereof).

In various embodiments when two cleavage monomers are used to form an active enzyme dimer, the recognition sites for the two zinc finger nucleases are preferably disposed such that binding of the two zinc finger nucleases to their respective recognition sites places the cleavage monomers in a spatial orientation to each other that allows the cleavage monomers to form an active enzyme dimer, e.g., by dimerizing. As a result, the near edges of the recognition sites may be separated by about 5 to about 18 nucleotides. For instance, the near edges may be separated by about 5, 6, 7, 8, 9, 10, 11, 12, 13, 14, 15, 16, 17 or 18 nucleotides. It will however be understood that any integral number of nucleotides or nucleotide pairs can intervene between two recognition sites (e.g., from about 2 to about 50 nucleotide pairs or more). The near edges of the recognition sites of the zinc finger nucleases, such as for example those described in detail herein, may be separated by 6 nucleotides. In general, the site of cleavage lies between the recognition sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme FokI catalyzes double-stranded cleavage of DNA, at 9 nucleotides from its recognition site on one strand and 13 nucleotides from its recognition site on the other (see, e.g., U.S. Pat. Nos. 5,356,802; 5,436,150, and 5,487,994; Li et al. (1992) *Proc. Natl. Acad. Sci. USA*, 89: 4275-4279; Li et al. (1993) *Proc. Natl. Acad. Sci. USA*, 90: 2764-2768. Thus, a zinc finger nuclease can comprise the cleavage domain from at least one Type IIS restriction enzyme and one or more zinc finger binding domains, which may or may not be engineered. Illustrative type IIS restriction enzymes are described for example in International Patent Publication No: WO 07/014,275. Additional restriction enzymes also contain separable binding and cleavage domains, and these also are contemplated by the present disclosure (see, e.g., Roberts et al. (2003) *Nucleic Acids Res.* 31:418-420.

An illustrative Type IIS restriction enzyme, whose cleavage domain is separable from the binding domain, is FokI. This particular enzyme is active as a dimer (Bitinaite et al.

(1998) *Proc. Natl. Acad. Sci. USA* 95: 10, 570-10, 575). Accordingly, for the purposes of the present disclosure, the portion of the FokI enzyme used in a zinc finger nuclease is considered a cleavage monomer. Thus, for targeted double-stranded cleavage using a FokI cleavage domain, two zinc finger nucleases, each comprising a FokI cleavage monomer, may be used to reconstitute an active enzyme dimer. Alternatively, a single polypeptide molecule containing a zinc finger binding domain and two FokI cleavage monomers can also be used.

In certain embodiments the cleavage domain may comprise one or more engineered cleavage monomers that minimize or prevent homodimerization, as described, for example, in U.S. Patent Publication Nos. 2005/0064474, 2006/0188987, 2008/0131962, and the like. By way of non-limiting example, amino acid residues at positions 446, 447, 479, 483, 484, 486, 487, 490, 491, 496, 498, 499, 500, 531, 534, 537, and 538 of FokI are all targets for influencing dimerization of the FokI cleavage half-domains. Illustrative engineered cleavage monomers of FokI that form obligate heterodimers include a pair in which a first cleavage monomer includes mutations at amino acid residue positions 490 and 538 of FokI and a second cleavage monomer that includes mutations at amino-acid residue positions 486 and 499 (see, e.g., Miller et al. (2007) *Nat. Biotechnol.* 25: 778-785; Szczpek et al. (2007) *Nat. Biotechnol.* 25: 786-793). For example, the Glu (E) at position 490 may be changed to Lys (K) and the Iie (I) at position 538 may be changed to K in one domain (E490K, I538K), and the Gin (Q) at position 486 may be changed to E and the I at position 499 may be changed to Leu (L) in another cleavage domain (Q486E, I499L). In other aspects, modified FokI cleavage domains can include three amino acid changes (see, e.g., Doyon et al. (2011) *Nat. Methods,* 8: 74-81). For example, one modified FokI domain (which is termed ELD) can comprise Q486E, I499L, N496D mutations and the other modified FokI domain (which is termed KKR) can comprise E490K, I538K, H537R mutations.

In certain embodiments the Zink finger protein can be modified to have an activator, a repressor, and/or an epigenetically modifying domain (e.g., in a manner similar to modified CRISPR constructs).

TALENs

In certain embodiments the targeted endonuclease comprises a Transcription Activator-Like Effector Nuclease (TALEN). TAL effector nucleases are a class of sequence-specific nucleases derived from *Xanthomonas* bacteria, that can be used to make double-strand breaks at specific target sequences in the genome of a prokaryotic or eukaryotic organism. The DNA binding domain of the TAL effector contains a repeated, highly conserved 33-34 amino acid sequence with the exception of the 12th and 13th amino acids. These two positions are highly variable, showing a strong correlation with specific nucleotide recognition. They can thus be engineered to bind to a desired DNA sequence.

TAL effector nucleases are created by fusing a native or engineered transcription activator-like (TAL) effector, or functional part thereof, to the catalytic domain of an endonuclease, such as, for example, FokI. The unique, modular TAL effector DNA binding domain allows for the design of proteins with potentially any given DNA recognition specificity. Thus, the DNA binding domains of the TAL effector nucleases can be engineered to recognize specific DNA target sites and thus, used to make double-strand breaks at desired target sequences (see, e.g., WO 2010/079430; Morbitzer et al. (2010) *Proc. Natl. Acad. Sci. USA,* 107(50): 21617-21622; Scholze & Boch (2010) *Virulence,* 1: 428-432; Christian et al. (2010) *Genetics,* 186:757-761; Li et al. (2010) *Nucl. Acids Res.* (1):359-372; and Miller et al. (2011) *Nat. Biotechl.* 29: 143-148).

To produce a TALEN, a TAL protein is fused to a nuclease, which is typically a wild-type or mutated FokI endonuclease. Several mutations to FokI have been made for its use in TALENs. These, for example, improve cleavage specificity or activity (see, e.g., Cermak et al. (2011) *Nucl. Acids Res.* 39: e82; Miller et al. (2011) *Nat. Biotech.* 29: 143-148; Hockemeyer et al. (2011) *Nat. Biotech.* 29: 731-734; Wood et al. (2011) *Science,* 333: 307; Doyon et al. (2010) *Nat. Meth.* 8: 74-79; Szczepek et al. (2007) *Nat. Biotech.* 25: 786-793; and Guo et al. (2010) *J Mol. Biol.* 200: 96).

The FokI domain functions as a dimer, typically requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity (see, e.g., Miller et al. (2011) *Nat. Biotech.,* 29: 143-148).

Examples of suitable TAL nucleases, and methods for preparing suitable TAL nucleases, are disclosed, e.g., in US Patent Application Nos. 2011/0239315 A1, 2011/0269234 A1, 2011/0145940 A1, 2003/0232410 A1, 2005/0208489 A1, 2005/0026157 A1, 2005/0064474 A1, 2006/0188987 A1, and 2006/0063231 A1. In various embodiments, TAL effector nucleases are engineered that cut in or near a target nucleic acid sequence in, e.g., a genomic locus of interest, where the target nucleic acid sequence is at or near a sequence to be modified by a targeting vector. In various embodiments, the TAL nucleases suitable for use with the various methods and compositions provided herein include those that are specifically designed to bind at or near target nucleic acid sequences to be modified, e.g., by targeting vectors.

In one illustrative, but non-limiting embodiment, each monomer of the TALEN comprises 10 or more DNA binding repeats, and in some cases 15 or more DNA binding repeats (e.g., in certain embodiments, 12-25 TAL repeats), wherein each TAL repeat binds a 1 bp subsite. In one embodiment, the nuclease agent is a chimeric protein comprising a TAL repeat-based DNA binding domain operably linked to an independent nuclease. In one embodiment, the independent nuclease is a Fok1 endonuclease (see e.g., Kim et al. (1996) *Proc. Natl. Acad. Sci. USA,* 93:1156-1160), however, other useful endonucleases may include, but are not limited to, for example, HhaI, HindIII, Nod, BbvCI, EcoRI, BglI, and AlwI.

In some embodiments, the TAL effector domain that binds to a specific nucleotide sequence within the target DNA comprises a plurality of repeat variable-diresidues (RVD) each of which determines recognition of a base pair in the target DNA sequence, where each DNA binding repeat is responsible for recognizing one base pair in the target DNA sequence, and wherein the RVD comprises one or more of: HD for recognizing C; NG for recognizing T; NI for recognizing A; NN for recognizing G or A; NS for recognizing A or C or G or T; N* for recognizing C or T, where * represents a gap in the second position of the RVD; HG for recognizing T; H* for recognizing T, where * represents a gap in the second position of the RVD; IG for recognizing T; NK for recognizing G; HA for recognizing C; ND for recognizing C; HI for recognizing C; HN for recognizing G; NA for recognizing G; SN for recognizing G or A; and YG for recognizing T.

If the genome editing endonuclease to be utilized is a TALEN, in some embodiments, optimal target sites may be selected in accordance with the methods described by Sanjana et al. (2012) *Nat. Protocol.*, 7: 171-192, which is hereby incorporated by reference in its entirety. In brief, in various embodiments, TALENs function as dimers, and a pair of TALENs, referred to as the left and right TALENs, target sequences on opposite strands of DNA. TALENs can be engineered as a fusion of the TALE DNA-binding domain and a monomeric FokI catalytic domain. In certain embodiments to facilitate FokI dimerization, the left and right TALEN target sites can be chosen with a spacing of approximately 14-20 bases. Therefore, for a pair of TALENs, each targeting 20-bp sequences, an optimal target site can have the form 5'-TN$^{19}$N$^{14-20}$N$^{19}$A-3', where the left TALEN targets 5'-TN$^{19}$-3' and the right TALEN targets the antisense strand of 5'-N$^{19}$A-3' (N=A, G, T or C). This is, of course illustrative and non-limiting and examples of TALENs that bind to particular target sites are well known to those of skill in the art. For more information on TALENs, refer to U.S. Pat. No. 8,685,737, which is hereby incorporated by reference in its entirety.

In certain embodiments the TALEs can be modified to have an activator, a repressor, and/or an epigenetically modifying domain (e.g., in a manner similar to modified CRISPR constructs).

The foregoing targeted endonucleases are illustrative and non-limiting. Using the teachings provided herein, gene drive constructs using other targeted endonucleases can readily be prepared by one of skill in the art.

EXAMPLES

The following examples are offered to illustrate, but not to limit the claimed invention.

Example 1

Illustrative Gene-Drive In a DNA Virus

In this example we describe a novel type of gene-drive in herpesviruses that doesn't involve sexual reproduction and show that it can drastically circumvent infection in human cells in vitro.

Herpesviruses are nuclear-replicating DNA viruses that harbor a large dsDNA genome (100-200 kb), encoding 100-200 genes (Louten (2016) Chapter 13, pp. 235-256 in Herpesviruses BT—Essential Human Virology, Academic Press, Boston). These properties enabled the design of a new gene drive strategy that doesn't involve sexual reproduction but relies on coinfection of a given cell by a wildtype and an engineered virus (see, e.g., FIG. 1, panel B). Upon coinfection, the wildtype genome is cleaved and repaired by homologous recombination, producing new gene drive viruses. Here we present a proof of concept for such a phenomenon, using human cytomegalovirus (hCMV) as a model. We showed that in cell culture experiments, gene drive viruses can replace their wildtype counterpart and spread in the viral population. We observed in cell culture experiments the successful transmission of a gene drive sequence between distinct strains of hCMV and showed that gene drive viruses can efficiently target and replace wildtype viruses. By targeting critical viral genes, our results indicate that viral gene drive could severely reduce viral infection. Importantly, hCMV cause life-threatening diseases in people with a compromised immune system, such as patient with AIDS, newborns, or the elderly (Griffiths et al. (2015) *J. Pathol.* 235: 288-297).

This example describes a novel type of gene drive in herpesviruses. The core of the invention is the ability to carry a gene drive sequence from the genome of an engineered virus to a wildtype one, thereby limiting the spread of wildtype viruses while creating new copies of the mutated one. As noted above, such a platform could be used as a cure to stop the spreading of infectious wildtype viruses. Of note, such a concept is not limited to herpesviruses and can readily be applied to any type of large DNA viruses.

Results

Here we demonstrate the successful transfer of a gene drive sequence between two different strains of human cytomegalovirus (hCMV). A gene drive donor plasmid targeting UL23, a viral gene involved in immune evasion (Feng et al. (2018) *PLOS Pathog.* 14: e1006867) (FIG. 1, panel C) was first constructed. The construct was flanked by homology arms and contained spCas9, one gRNA against UL23 locus, and an mCherry fluorescent reporter.

Human foreskin fibroblasts (HFF) were transfected by nucleofection with the gene drive construct. After 24 hours, cells were infected at low multiplicity of infection (MOI=0.1) with TB40/E-bac4, a wildtype hCMV strain (Sinzger et al. (2008) *J Gen. Virol.* 89: 359-368). After 7-10 days, red plaques of mCherry expressing cells could be observed (FIG. 2, panel A). mCherry-expressing viruses creating these plaques were isolated and purified by several rounds of plaque purifications and serial dilutions, until a pure population of mCherry-expressing viruses could be obtained. PCR across homology arms and sequencing confirmed that these mCherry-expressing viruses contained the full gene drive sequence (FIG. 2, panel B). This indicated that infectious gene drive viruses were successfully created by homologous recombination.

Figure 3:
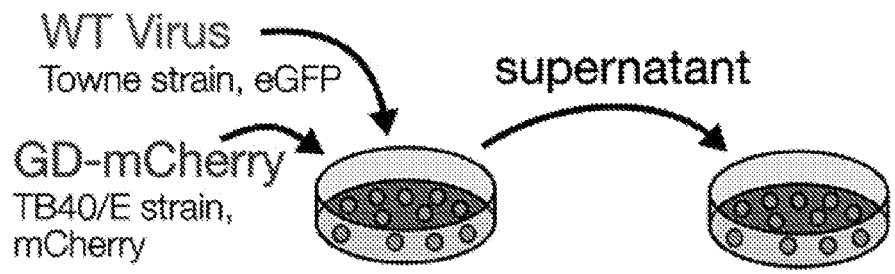
FIG. 3, panels A-F, illustrates recombination of the gene drive cassette into the wildtype genome. Panel A) Co-infection of fibroblasts with mCherry-expressing GD-UL79 virus (TB40/E strain) and eGFP-expressing WT virus (Towne-strain). Panel B) Representative examples of fluorescent viral plaques spreading on fibroblasts. Panel C) PCR for mCherry (upper band) and eGFP (lower band) on 48 recombinant clones. Panel D) PCR of homology arms and Sanger sequencing of 17 eGFP-mCherry expressing clones. Squares: SNPs from Towne strain; Circles: TB40/E strain. For clones 1, 28, 29 and 43, the figure shows that the gene drive cassette originally from a TB40/E strain is now located near regions from Towne strain. Panel E) Viral titer and proportion of viruses expressing eGFP alone, mCherry alone, or both as measured by plaque assay. The figure shows that gene drive viruses (mCherry and eGFP-mCherry) invade and replace the wildtype population (eGFP). 4 Biological replicates. Panel F) Viral titer at day 10 in presence of increasing concentration of IFN-γ. 3-5 biological replicates.
Figure 3:
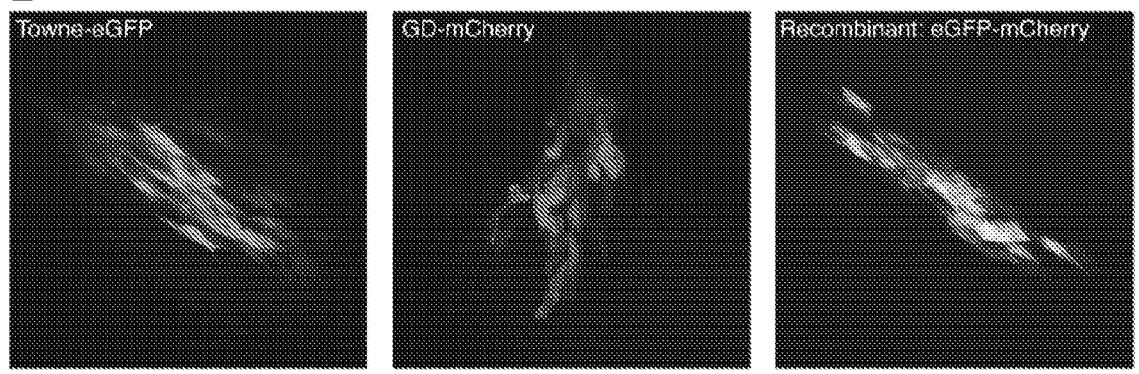
Figure 3:
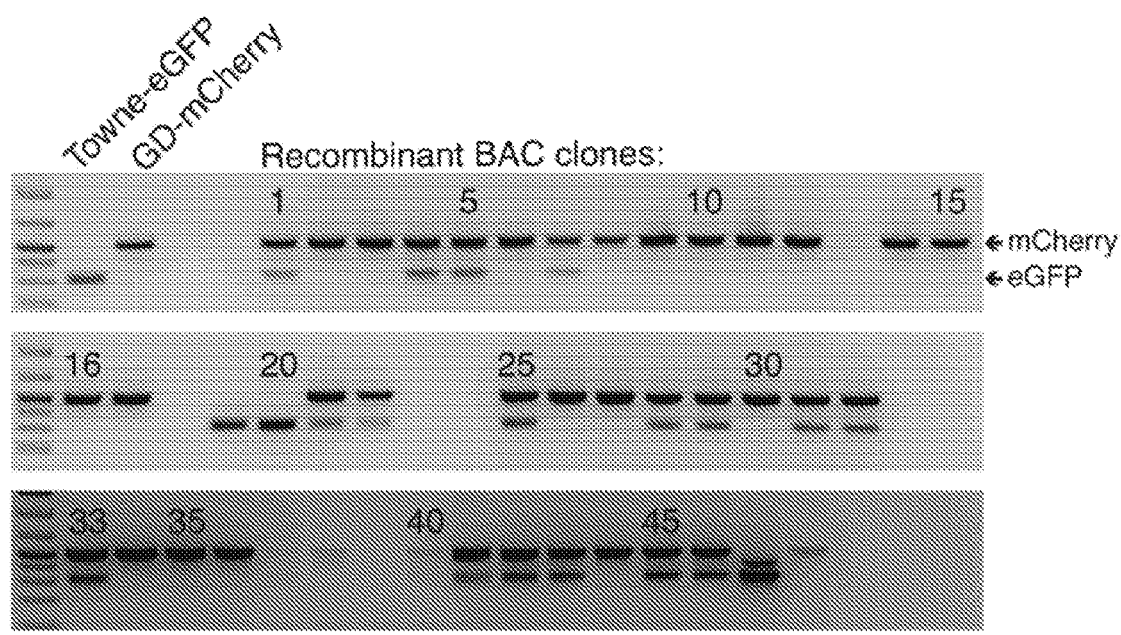

To assess whether gene drive viruses could recombine with wild type viruses, HFF cells were then co-infected at low MOI with: 1) the mCherry-expressing gene drive viruses (TB40/E strain); 2) an eGFP-expressing wildtype virus (Towne-strain) (Marchini et al. (2001) *J Virol.* 75: 1870-1878). Supernatant of co-infected cells was then used to infect fresh HFF at a very low MOI (FIG. 3, panel A). We could detect cells and viral plaques expressing either eGFP alone, mCherry alone, or mCherry and eGFP together (FIG. 3, panel B). Furthermore, mCherry-eGFP expressing cells formed spreading viral plaques, suggesting that both mCherry and eGFP are inserted in the same viral genome.

Figure 4:
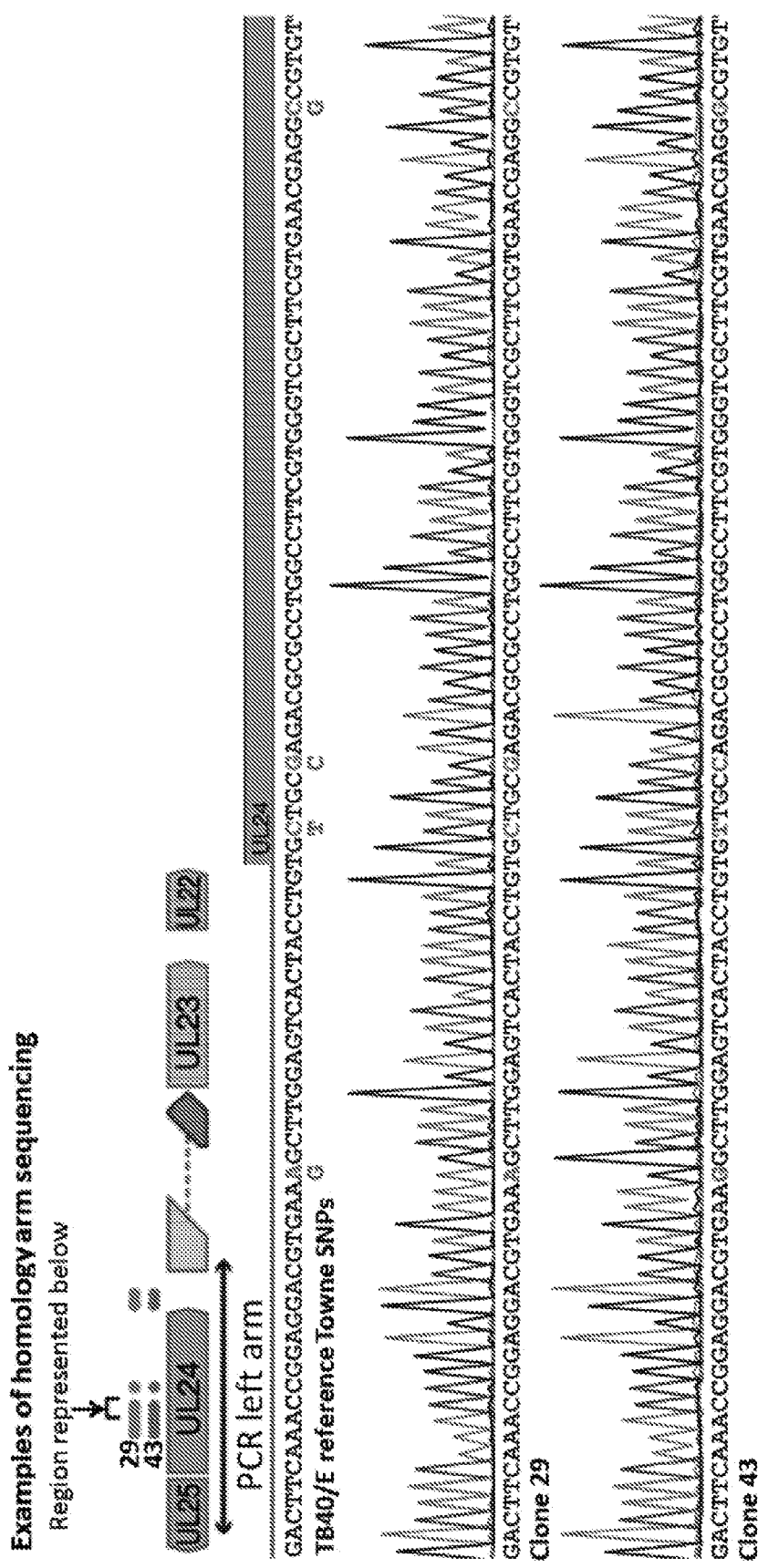
FIG. 4 illustrates Sanger sequencing of homology arms. Example of Sanger sequencing of the left homology arm of two recombinant clones. Clone 29 harbor SNPs from TB40/E strain, while clone 43 has SNPs from Towne strain. TB40/E reference Towne SNPs (SEQ ID NO:3), Clone 29 (SEQ ID NO:4), clone 43 (SEQ ID NO:5).

Multiple recombinant genomes were isolated, and we showed by PCR that mCherry and eGFP were present in the same viral genome (FIG. 3, panel C). Sanger sequencing of homology arms finally demonstrated that the gene drive sequence has been transferred from the TB40/E strain to the Towne strain. (FIG. 3, panel D, FIG. 4).

We then showed that gene drive viruses could spread into the viral population and replace wildtype viruses (FIG. 3, panel E). Moreover, because gene drive viruses are knockout for UL23, a viral gene involved into Interferon gamma immune evasion, infectivity of gene drive viruses is severely reduced in presence of interferon gamma (FIG. 3, panel F).

Figure 5:
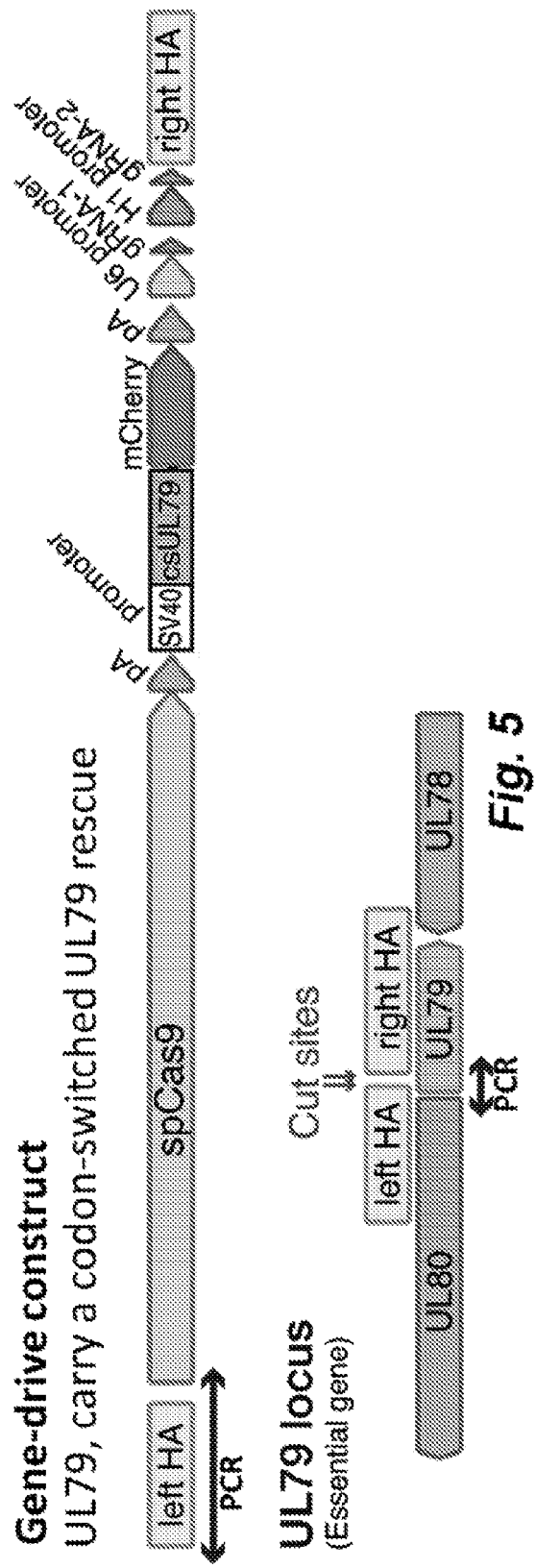
FIG. 5 illustrates a gene drive construct against UL79. The illustrated gene drive construct targets the UL79 locus and is composed of spCas9 (under UL79 native viral promoter), mCherry, and a codon-switched rescue of UL79 separated by an auto-cleavable T2A peptide (under the control of an SV40 promoter), two gRNAs (under U6 and H1 promoters, respectively).

Another gene drive system against the critical viral gene UL79 was also generated and showed to work similarly (FIG. 5). UL79 is a viral gene essential for hCMV replication (Chapa et al. (2013) *J Virol.* 87: 9135-9147; Isomura et al. (2011) *J Virol.* 85: 6629-6644). The construct was flanked by homology arms and contained spCas9 sequence, two gRNAs against UL79 locus, and an mCherry fluorescent reporter. Moreover, since knocking-out UL79 would prevent the production of infectious virions, the gene drive construct also contained a codon-switched rescue of the UL79 coding sequence. This ensured that UL79 gene drive viruses (GD-UL79) would be infectious. We however noted that that GD-UL79 infectivity was severely reduced. We showed similarly that GD-UL79 could recombine and replace wild-type viruses.

Methods

Plasmid Construction.

The gene drive donor plasmid (pGD-UL23) was built upon pU6-(Bbsl)_CBh-Cas9-T2A-mCherry (Addgene plasmid #64324), a modification of pX330 (Addgene plasmid #42230 from the Feng Zhang lab) (Chu et al. (2015) *Nat. Biotechnol.* 33: 543-548; Le Cong et al. (2013) *Science*, 339: 819-823). First, a left homology arm was amplified by PCR from viral DNA (Towne-strain) and inserted by Gibson cloning upstream of SpCaS9 cDNA, replacing U6 and CBh sequences from pU6-(Bbsl)_CBh-Cas9-T2A-mCherry. Second, a fragment containing one gRNAs against UL23 (under U6 promoter) and the right homology arm was synthesized (geneArt gene synthesis from ThermoFisher) and inserted by Gibson cloning downstream of beta globin polyA.

Gene drive against UL79 was constructed similarly, with two gRNA targeting UL79 (with a U6 and H1 promoter, respectively). A fragment containing a SV40 polyA sequence, a SV40 promoter and a codon switched UL79 cDNA was synthesized (geneArt gene synthesis from ThermoFisher) and inserted by Gibson cloning between spCas9 and mCherry.

Virus and Cell Lines.

hCMV TB40/E-Bac4 (Sinzger et al. (2008) *J Gen. Virol.* 89: 359-368) and Towne-eGFP (TBACwt) (Marchini et al. (2001) *J Virol.* 75: 1870-1878) were kindly provided by Edward Mocarski (Emory University, USA). To prepare viral stocks, cells were infected at low MOI (0001-001) and kept in culture until 100% cytopathic effect (CPE) was observed, usually after 10-15 days. Cells were then scraped out of the plate and centrifugated together with the supernatant (10,000 rpm-1 h-4° C.), resuspended in media containing 5% milk, and sonicated to release cell-bound virions. Viral titers were assessed by plaque assay. Except when otherwise specified, subsequent infections were performed for one hour at MOI=0.1, before replacing inoculum with fresh medium.

Susceptibility to IFN-gamma (IFN-γ) was assayed by virus growth in the presence of human recombinant IFN-γ (R&D, Minneapolis, USA) after preincubating for 2 hours before infection. Viral titers were assayed by plaque assay with 10-fold serial dilutions. 24-wells plates were inoculated for one hour and overlaid with 0.25% agarose. After 7-10 days, eGFP or mCherry fluorescent plaques were manually counted using an inverted microscope. Every viral plaque was analyzed on both green and red channel. 5-100 plaques were counted per well, and each data-point was the average of 3-4 technical replicates (i.e., 3-4 different wells).

Coinfection experiments were performed by coinfecting with wildtype Towne-eGFP and gene drive viruses for one hour, with a total MOI around 0.1-0.2. For time course experiments over multiple weeks, supernatants were used to inoculate fresh cells for one hour before changing media.

Generation of Gene Drive Virus.

1.5 µg of plasmid pGD-U79 were transfected into 1.5 million HFF cell by nucleofection (P2 Primary Cell 4D-Nucleofector™ kit from Lonza, program DT-130) and plated into 3 different wells (0.5 million cells per well). After 24 hours, cells were infected for one hour with TB40/E virus at various MOI (0.1, 0.2 and 0.5, respectively). After 7-10 days, viral plaques expressing mCherry were isolated and plated into fresh HFF, and further purified by several rounds of plaques purifications and serial dilutions.

Integration of the gene drive construct into UL23 locus was verified by PCR using the following primers: GCGACGACGATCGTTTCTTT (SEQ ID NO:36) and CTTGTAGTCTCCGTCGTGGT (SEQ ID NO:37) (left homology arm); CAACTTGAAAAAGTGGCACCGA (SEQ ID NO:38) and TTGTGAACGCGGTTATCGTG (SEQ ID NO:39) (right homology arm, not shown here); GCTTGGGGCATAAAACACCG (SEQ ID NO:40) and CCCAGGTACAGTTCAGACGG (SEQ ID NO:41) (PCR across the cut site).

DISCUSSION

These results demonstrated that a gene-drive system can be successfully implemented in herpesviruses and by implication, other DNA viruses. The data show that when cells are co-infected with a gene-drive and a wildtype virus, the wildtype genome can be converted into a new gene-drive genome, thereby ensuring the spread of new gene-drive viruses. These first gene-drive viruses were constructed as a proof of concept.

Various gene drive systems that would stop the infection and could be used as a new therapeutic strategy can be similarly created. Therapeutic gene-drives would follow the same basic principle as the one presented above. Gene drive constructs that knock-out essential viral genes can be constructed. Typically, the genome of these gene-drive viruses will lack an essential viral gene (replaced by Cas9 and gRNAs), preventing the production of infectious virions. However, upon co-infection by a gene-drive and a wildtype virus, new infectious gene-drive virions could be produced using the gene products of the wildtype genome. Concomitantly, the expression of Cas9 from the gene-drive genome would inactivate the wildtype virus and convert it into new gene-drive genome.

This strategy relies, inter alia, on the dynamics of expression of Cas9 or other endonuclease (from the gene-drive genome) and the corresponding wildtype gene. Enough wildtype protein should be produced from the wildtype genome before Cas9 is expressed and inactivates it.

Accordingly, in certain embodiments, gene-drive constructs can be provided against several hCMV genes, each expressed at different time of the virus life cycle: UL122 (immediate-early expression), UL79 (early-late expression), UL99 and UL55 (true-late expression). This system would allow the production of novel gene-drive viruses and would stop the infection once every wildtype virus has been converted or inactivated.

This represents a novel therapeutic strategy against hCMV or other herpesviruses for which there is currently no available treatment, like HHV-8 (Kaposi's sarcoma-associated herpesviruses).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of modifying a target DNA virus, said method comprising:
    transfecting or infecting a cell population with a modified DNA virus containing a gene drive construct; and
    infecting said cell population with said target DNA virus
    wherein the genome of said target DNA virus is modified by insertion of said gene drive construct into the genome of said target DNA virus thereby producing a modified target virus,
    wherein said target DNA virus and said modified DNA virus are the same species of DNA virus.

2. The method of claim 1, wherein:
    said target DNA virus comprises a genome large enough to add a 6-7 kb gene drive sequence; and/or
    said target DNA virus has a minimal viral genome size of about 50 kb; and/or
    said target DNA virus has the capacity to undergo homologous recombination; and/or
    said target DNA virus comprises a nuclear-replicating virus.

3. The method of claim 1, wherein:
    said target DNA virus and said modified DNA virus are from a viral family selected from the group consisting of Herpesviridae, Alloherpesviridae, Malacoherpesviridae, Lipothrixviridae, Rudiviridae, Adenoviridae, Ampullaviridae, Ascoviridae, Asfarviridae, Baculoviridae, Bicaudaviridae, Clavaviridae, Corticoviridae, Fuselloviridae, Globuloviridae, Guttaviridae, Hytrosaviridae, Iridoviridae, Lavidaviridae, Marseilleviridae, Mimiviridae, Nudiviridae, Nimaviridae, Pandoraviridae, Papillomaviridae, Phycodnaviridae, Plasmaviridae, Polydnaviruses, Polyomaviridae, Poxviridae, Sphaerolipoviridae, Tectiviridae, and Turriviridae; or
    said target DNA virus and said modified DNA virus are from the Herpesviridae family; or
    said target DNA virus and said modified DNA virus are selected from the group consisting of HHV-5 (cytomegalovirus), HHV-1, HHV-2, HHV-3 (varicella-zoster virus (VZV)), HHV-4 (Epstein-Barr virus (EBV)), HHV-6A and 6B, HHV-7, and HHV-8 (Kaposi's sarcoma-associated herpesvirus (KSHV)), C3Hv, CeHV-1, MuHV-4, SuHV1, BoHV-1, GaHV-1, and MDV; or
    said target DNA virus and said modified DNA virus are selected from the group consisting of HHV-5 (cytomegalovirus), HHV-1, HHV-2, HHV-3 (varicella-zoster virus (VZV)), HHV-4 (Epstein-Barr virus (EBV)), HHV-6A and 6B, HHV-7, and HHV-8 (Kaposi's sarcoma-associated herpesvirus (KSHV)); or
    said target DNA virus and said modified DNA virus are HHV-5; or
    said target DNA virus and said modified DNA virus are adenovirus; or
    said target DNA virus and said modified DNA virus are baculovirus.

4. The method of claim 1, wherein:
    said target DNA virus and said modified DNA virus are selected from the group consisting of Ascoviridae, Asfarviridae, Poxviridae, Iridoviridae, Marseilleviridae, Megaviridae, Pandoraviridae, Phycodnaviridae, and Pithoviridae; or
    said target DNA virus and said modified DNA virus is a poxvirus or an African Swine fever virus.

5. The method of claim 1, wherein said gene drive construct comprises a nucleic acid encoding a targeted endonuclease inserted into the genome of the modified DNA virus at a location corresponding to the location in the target DNA virus that is cleaved by said targeted endonuclease.

6. The method of claim 5, wherein said gene drive construct comprises homology arms that permit insertion of said gene drive construct at a site cleaved by said endonuclease.

7. The method of claim 5, wherein said targeted endonuclease comprises an endonuclease selected from the group consisting of a class 2 CRISPR/Cas endonuclease, a TALEN, and a zinc finger nuclease.

8. The method of claim 7, wherein said targeted endonuclease comprises a class 2 CRISPR/Cas endonuclease and said gene drive construct further comprise a nucleic acid encoding a guide RNA.

9. The method of claim 8, wherein the class 2 CRISPR/Cas endonuclease comprises a Cas9 protein.

10. The method of claim 8, wherein said class 2 CRISPR/Cas endonuclease is a type V or type VI CRISPR/Cas endonuclease.

11. The method of claim 10, wherein the class 2 CRISPR/Cas protein is selected from the group consisting of a Cpf1 polypeptide or a functional portion thereof, a C2c1 polypeptide or a functional portion thereof, a C2c3 polypeptide or a functional portion thereof, and a C2c2 polypeptide or a functional portion thereof.

12. The method of claim 8, wherein said gene drive construct encodes at least one guide RNA, wherein said guide RNA directs said targeted endonuclease to a site in the genome of said target DNA virus where cleavage permits integration of said gene drive construct by homologous recombination.

13. The method of claim 1, wherein said gene drive construct inserts into and disrupts a gene essential for viral infection and/or replication.

14. The method of claim 1, wherein: said gene drive construct introduces a modification that inhibits replication and/or assembly of said target DNA virus and said modification is compensated for by expression of a gene by the unmodified target DNA virus in said cell to permit viral replication of the modified target DNA virus; or said gene drive construct introduces a modification that inhibits replication and/or assembly of said target DNA virus and said modification is compensated for by expression of a rescue gene within said gene drive construct allowing for replication and assembly of the modified target DNA virus.

15. The method of claim 1, wherein said modified DNA virus and said target DNA virus are introduced into the cell population ex vivo.

16. The method of claim 1, wherein said method comprises administering said modified DNA virus to an animal already infected with said target DNA virus whereby the modified DNA virus infects a cell population already infected with said target DNA virus.

17. The method of claim 1, wherein said gene drive construct comprises a nucleic acid encoding a homing endonuclease inserted into the genome of the modified DNA virus at a location corresponding to the location in the target DNA virus that is cleaved by said homing endonuclease.

* * * * *

SEQUENCE LISTING

<160> NUMBER OF SEQ ID NOS: 18

<210> SEQ ID NO 1
<211> LENGTH: 114
<212> TYPE: DNA
<213> ORGANISM: human cytomegalovirus

<400> SEQUENCE: 1
tttccggatc ggcccgattt cttttttgtcc accgacgcgc gaccgcgatg tcggtaatca    60
aggactgttt tctcaatctg ctcgaccgct ggaggcctcc taagacgtcg cgac           114

<210> SEQ ID NO 2
<211> LENGTH: 113
<212> TYPE: DNA
<213> ORGANISM: artificial
<220> FEATURE:
<223> OTHER INFORMATION: Modified cytomegalovirus

<400> SEQUENCE: 2
tttccggatc ggcccgattt cttttttgtac cggtgccacc atcgactata aggaccacga    60
cggagactac aaggatcatg atattgatta caaagacgat gacgataaga tgg            113

<210> SEQ ID NO 3
<211> LENGTH: 94
<212> TYPE: DNA
<213> ORGANISM: artificial
<220> FEATURE:
<223> OTHER INFORMATION: CRISPR cut site

<400> SEQUENCE: 3
gacttcaaac cggaggacgt gaaagcttgg agtcactacc tgtgctgcga gacgcgcctg    60
gccttcgtgg gtcgcttcgt gaacgaggcc gtgt                                94

<210> SEQ ID NO 4
<211> LENGTH: 94
<212> TYPE: DNA
<213> ORGANISM: artificial
<220> FEATURE:
<223> OTHER INFORMATION: CRISPR cut site

<400> SEQUENCE: 4
gacttcaaac cggaggacgt gaaagcttgg agtcactacc tgtgctgcga gacgcgcctg    60
gccttcgtgg gtcgcttcgt gaacgaggcc gtgt                                94

<210> SEQ ID NO 5
<211> LENGTH: 94
<212> TYPE: DNA
<213> ORGANISM: artificial
<220> FEATURE:
<223> OTHER INFORMATION: CRISPR cut site

<400> SEQUENCE: 5
gacttcaaac cggaggacgt gaaggcttgg agtcactacc tgtgttgcca gacgcgcctg    60
gccttcgtgg gtcgcttcgt gaacgagggc gtgt                                94

<210> SEQ ID NO 6
<211> LENGTH: 20
<212> TYPE: DNA
<213> ORGANISM: artificial
<220> FEATURE:
<223> OTHER INFORMATION: CRISPR guide sequence

```
<400> SEQUENCE: 6
tagatgattg gcgcaagtaa                                              20

<210> SEQ ID NO 7
<211> LENGTH: 20
<212> TYPE: DNA
<213> ORGANISM: artificial
<220> FEATURE:
<223> OTHER INFORMATION: CRISPR guide sequence

<400> SEQUENCE: 7
attagcgaga agatgtcgcg                                              20

<210> SEQ ID NO 8
<211> LENGTH: 20
<212> TYPE: DNA
<213> ORGANISM: artificial
<220> FEATURE:
<223> OTHER INFORMATION: CRISPR guide sequence

<400> SEQUENCE: 8
ttggaggaag ggccctcgtc                                              20

<210> SEQ ID NO 9
<211> LENGTH: 20
<212> TYPE: DNA
<213> ORGANISM: artificial
<220> FEATURE:
<223> OTHER INFORMATION: CRISPR guide sequence

<400> SEQUENCE: 9
atcagggtcc atctttctct                                              20

<210> SEQ ID NO 10
<211> LENGTH: 20
<212> TYPE: DNA
<213> ORGANISM: artificial
<220> FEATURE:
<223> OTHER INFORMATION: CRISPR guide sequence

<400> SEQUENCE: 10
gcgacccaga gcatctttca                                              20

<210> SEQ ID NO 11
<211> LENGTH: 20
<212> TYPE: DNA
<213> ORGANISM: artificial
<220> FEATURE:
<223> OTHER INFORMATION: CRISPR guide sequence

<400> SEQUENCE: 11
ccgacttcct cctcggacga                                              20

<210> SEQ ID NO 12
<211> LENGTH: 20
<212> TYPE: DNA
<213> ORGANISM: artificial
<220> FEATURE:
<223> OTHER INFORMATION: CRISPR guide sequence
```

```
<400> SEQUENCE: 12
ggacgacctc atgagcggcc                                                   20

<210> SEQ ID NO 13
<211> LENGTH: 20
<212> TYPE: DNA
<213> ORGANISM: artificial
<220> FEATURE:
<223> OTHER INFORMATION: CRISPR guide sequence

<400> SEQUENCE: 13
aaggccgttg gcgtagccat                                                   20

<210> SEQ ID NO 14
<211> LENGTH: 20
<212> TYPE: DNA
<213> ORGANISM: artificial
<220> FEATURE:
<223> OTHER INFORMATION: CRISPR guide sequence

<400> SEQUENCE: 14
acatcgcggt cgcgcgtcgg                                                   20

<210> SEQ ID NO 15
<211> LENGTH: 20
<212> TYPE: DNA
<213> ORGANISM: artificial
<220> FEATURE:
<223> OTHER INFORMATION: CRISPR guide sequence

<400> SEQUENCE: 15
gtccttgatt accgacatcg                                                   20

<210> SEQ ID NO 16
<211> LENGTH: 20
<212> TYPE: DNA
<213> ORGANISM: artificial
<220> FEATURE:
<223> OTHER INFORMATION: CRISPR guide sequence

<400> SEQUENCE: 16
tcaatctgct cgaccgctgg                                                   20

<210> SEQ ID NO 17
<211> LENGTH: 20
<212> TYPE: DNA
<213> ORGANISM: artificial
<220> FEATURE:
<223> OTHER INFORMATION: CRISPR guide sequence

<400> SEQUENCE: 17
ttctcaatct gctcgaccgc                                                   20

<210> SEQ ID NO 18
<211> LENGTH: 20
<212> TYPE: DNA
<213> ORGANISM: artificial
<220> FEATURE:
<223> OTHER INFORMATION: CRISPR guide sequence

<400> SEQUENCE: 18
caaaaagaca tcgaggcata                                                   20
```